United States Patent
Wu et al.

(10) Patent No.: US 11,668,718 B2
(45) Date of Patent: Jun. 6, 2023

(54) PEPTIDE QUANTITATION ASSAY FOR DIFFERENTIATING FULL-LENGTH HIGH MOLECULAR WEIGHT KININOGEN (HMWK) AND CLEAVED HMWK

(71) Applicant: Takeda Pharmaceutical Company Limited, Osaka (JP)

(72) Inventors: Jiang Wu, Lexington, MA (US); Guodong Zhang, Lexington, MA (US); Daniel J. Sexton, Melrose, MA (US); Ryan Faucette, Melrose, MA (US); Gul M. Mustafa, Morgantown, WV (US); Mark Szewc, Morgantown, WV (US)

(73) Assignee: Takeda Pharmaceutical Company Limited, Osaka (JP)

( * ) Notice: Subject to any disclaimer, the term of this patent is extended or adjusted under 35 U.S.C. 154(b) by 755 days.

(21) Appl. No.: 16/062,734

(22) PCT Filed: Dec. 15, 2016

(86) PCT No.: PCT/US2016/066936
§ 371 (c)(1),
(2) Date: Jun. 15, 2018

(87) PCT Pub. No.: WO2017/106504
PCT Pub. Date: Jun. 22, 2017

(65) Prior Publication Data
US 2021/0025898 A1    Jan. 28, 2021

Related U.S. Application Data

(60) Provisional application No. 62/267,734, filed on Dec. 15, 2015.

(51) Int. Cl.
*G01N 33/68* (2006.01)
*G01N 30/72* (2006.01)
(Continued)

(52) U.S. Cl.
CPC ..... *G01N 33/6848* (2013.01); *G01N 30/7233* (2013.01); *G01N 30/88* (2013.01);
(Continued)

(58) Field of Classification Search
None
See application file for complete search history.

(56) References Cited

U.S. PATENT DOCUMENTS 5,047,323 A    9/1991 Colman et al.
2006/0154319 A1    7/2006 Flodgaard et al.
(Continued)

FOREIGN PATENT DOCUMENTS

CN    1858243 A    11/2006
CN    102558329 A    7/2012
(Continued)

OTHER PUBLICATIONS

Salvesen et al., Human low-Mr kininogen contains three copies of a cystatin sequence that are divergent in structure and in inhibitory activity for cysteine proteinases. Biochem J. Mar. 1, 1986;234(2):429-34.
(Continued)

*Primary Examiner* — Xiaoyun R Xu
(74) *Attorney, Agent, or Firm* — Wolf, Greenfield & Sacks, P.C.

(57) ABSTRACT

Methods for differentiating full-length high molecular weight kininogen (HMWK) and cleaved HMWK in a sample are provided herein. Such methods may comprise treating a biological sample with a protease to generate a plurality of digested peptides, and measuring one or more signature peptides, which are indicative of cleaved HMWK and/or full-length HMWK.

14 Claims, 7 Drawing Sheets

Specification includes a Sequence Listing.

(51) Int. Cl.
*G01N 30/88* (2006.01)
*G01N 30/02* (2006.01)

(52) U.S. Cl.
CPC ... *G01N 33/6893* (2013.01); *G01N 2030/027* (2013.01); *G01N 2030/8831* (2013.01); *G01N 2800/224* (2013.01); *G01N 2800/50* (2013.01)

(56) References Cited

U.S. PATENT DOCUMENTS

| | | | |
|---|---|---|---|
| 2010/0209940 | A1 | 8/2010 | Veidal et al. |
| 2011/0129859 | A1 | 6/2011 | Tsubouchi et al. |
| 2015/0050270 | A1 | 2/2015 | Li et al. |

FOREIGN PATENT DOCUMENTS

| | | | | |
|---|---|---|---|---|
| CN | 104155457 | A | | 11/2014 |
| CN | 104345154 | A | | 2/2015 |
| CN | 105073778 | A | | 11/2015 |
| EP | 0 787 499 | A1 | | 8/1997 |
| EP | 2 216 651 | A1 | | 8/2010 |
| JP | H01140065 | A | | 6/1989 |
| JP | H08208692 | A | | 8/1996 |
| JP | 2012-073190 | A | | 4/2012 |
| WO | WO 2000/027415 | A2 | | 5/2000 |
| WO | WO 2001/034195 | A1 | | 5/2001 |
| WO | WO 2003/077872 | A2 | | 9/2003 |
| WO | WO 2009/051259 | A1 | | 4/2009 |
| WO | WO 2010/004962 | A1 | | 1/2010 |
| WO | WO 2010/060636 | A1 | | 6/2010 |
| WO | WO 2014/113712 | A1 | | 7/2014 |
| WO | WO 2015/025975 | A1 | | 2/2015 |
| WO | WO 2015/061183 | A1 | | 4/2015 |
| WO | WO 2015/120036 | | * 8/2015 | ............ G01N 24/00 |
| WO | WO 2016/081413 | A1 | | 5/2016 |

OTHER PUBLICATIONS

Hänninen et al., Interleukin-2 based home therapy of metastatic renal cell carcinoma: risks and benefits in 215 consecutive single institution patients. J Urol. Jan. 1, 1996;155(1):19-25.

Yang et al., Inhibition of Cell Spreading by Recombinant Histidine-rich Domain of High Molecular Weight Kininogen and Its Mechanism. Chinese Journal of Biochemistry and Molecular Biology. Jan. 2003;19(2):222-228.

Zhang et al., 2D-LC-MS/MS to measure cleaved high-molecular-weight kininogen in human plasma as a biomarker for C1-INH-HAE. Bioanalysis. Oct. 2017;9(19):1477-1491. doi: 10.4155/bio-2017-0105. Epub Oct. 21, 2017.

Asakura et al., Inhibition of cell adhesion by high molecular weight kininogen. J Cell Biol. Jan. 1992;116(2):465-76. doi: 10.1083/jcb.116.2.465.

Damasceno et al., Bradykinin release avoids high molecular weight kininogen endocytosis. PLoS One. Mar. 30, 2015;10(3): e0121721. doi: 10.1371/journal.pone.0121721.

Kamiyama et al., Inhibition of vitronectin-mediated haptotaxis and haptoinvasion of MG-63 cells by domain 5 (D5(H)) of human high-molecular-weight kininogen and identification of a minimal amino acid sequence. Biochem Biophys Res Commun. Nov. 9, 2001;288(4):975-80. doi: 10.1006/bbrc.2001.5864.

Katcher et al., A simple and rapid method to study the association of the contact proteins of blood coagulation. Thrombosis research. Dec. 15, 1992;68(6):443-50.

Kunapuli et al., Deletion mutagenesis of high molecular weight kininogen light chain. Identification of two anionic surface binding subdomains. J Biol Chem. Feb. 5, 1993;268(4):2486-92.

Tait et al., Primary structure requirements for the binding of human high molecular weight kininogen to plasma prekallikrein and factor XI. J Biol Chem. Aug. 25, 1987;262(24):11651-6.

Zhang et al., Two-chain high molecular weight kininogen induces endothelial cell apoptosis and inhibits angiogenesis: partial activity within domain 5. FASEB. Dec. 2000;14(15):2589-600.

Zhang et al., Recent advances in absolute quantification of peptides and proteins using LC-MS. Reviews in Analytical Chemistry. Feb. 13, 2014;33(1):31-47. doi: 10.1515/revac-2013-0019.

* cited by examiner

| Peptides | HK_enzyme research | HK_Sigma | Plasma EDTA | Plasma Citrate (PI) | Plasma Citrate |
|---|---|---|---|---|---|
| SSRIGE | Y | Y | Y | Y | Y |
| SSRIGEIKE mis 2 | N | N | N | N | N |
| KKIYPTVNCQPLGMISLMK | N | N | Y | Y | Y |
| Long HK peptide | Y | Y | N | N | Y |
| SYYD-DGLS | Y | Y | N | N | Y |
| INPT-QMKE | Y | Y | N | N | Y |
| KQRH-HKE | Y | Y | Y | Y | Y |
| LMWK | N | N | Y | N | Y |

Digestion_25°C / Digestion_37°C

▨ Present
☐ Absent

SEQUENCE LISTING

```
<160> NUMBER OF SEQ ID NOS: 30

<210> SEQ ID NO 1
<211> LENGTH: 8
<212> TYPE: PRT
<213> ORGANISM: Artificial Sequence
<220> FEATURE:
<223> OTHER INFORMATION: Synthetic Polypeptide
```

<400> SEQUENCE: 1

Lys His Asn Leu Gly His Gly His
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 2

Lys His Asn Leu Gly His Gly His Lys His Glu
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 3

Lys His Asn Leu Gly His Gly His Lys
1               5

<210> SEQ ID NO 4
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 4

Lys His Asn Leu Gly His Gly His Lys His Glu Arg
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 5

Ser Ser Arg Ile Gly Glu
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 6

Gly His Glu Lys Gln Arg Lys His
1               5

<210> SEQ ID NO 7
<211> LENGTH: 14
<212> TYPE: PRT
<213> ORGANISM: Artificial Sequence
<220> FEATURE:
<223> OTHER INFORMATION: Synthetic Polypeptide

```
<400> SEQUENCE: 7

Lys Gln Arg Lys His Asn Leu Gly His Gly His Lys His Glu
1               5                   10

<210> SEQ ID NO 8
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 8

Asp Trp Gly His Lys Gln Arg Lys His Asn Leu Gly His Gly His Lys
1               5                   10                  15

His Glu Arg

<210> SEQ ID NO 9
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 9

His Asn Leu Gly His Gly His Lys
1               5

<210> SEQ ID NO 10
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 10

Ser Tyr Tyr Phe Asp Leu Thr Asp Gly Leu Ser
1               5                   10

<210> SEQ ID NO 11
<211> LENGTH: 644
<212> TYPE: PRT
<213> ORGANISM: Homo sapiens

<400> SEQUENCE: 11

Met Lys Leu Ile Thr Ile Leu Phe Leu Cys Ser Arg Leu Leu Leu Ser
1               5                   10                  15

Leu Thr Gln Glu Ser Gln Ser Glu Glu Ile Asp Cys Asn Asp Lys Asp
                20                  25                  30

Leu Phe Lys Ala Val Asp Ala Ala Leu Lys Lys Tyr Asn Ser Gln Asn
            35                  40                  45

Gln Ser Asn Asn Gln Phe Val Leu Tyr Arg Ile Thr Glu Ala Thr Lys
        50                  55                  60

Thr Val Gly Ser Asp Thr Phe Tyr Ser Phe Lys Tyr Glu Ile Lys Glu
65                  70                  75                  80

Gly Asp Cys Pro Val Gln Ser Gly Lys Thr Trp Gln Asp Cys Glu Tyr
                85                  90                  95

Lys Asp Ala Ala Lys Ala Ala Thr Gly Glu Cys Thr Ala Thr Val Gly
            100                 105                 110

Lys Arg Ser Ser Thr Lys Phe Ser Val Ala Thr Gln Thr Cys Gln Ile
        115                 120                 125

Thr Pro Ala Glu Gly Pro Val Val Thr Ala Gln Tyr Asp Cys Leu Gly
```

```
               130                 135                 140
Cys Val His Pro Ile Ser Thr Gln Ser Pro Asp Leu Glu Pro Ile Leu
145                 150                 155                 160

Arg His Gly Ile Gln Tyr Phe Asn Asn Asn Thr Gln His Ser Ser Leu
                165                 170                 175

Phe Met Leu Asn Glu Val Lys Arg Ala Gln Arg Gln Val Val Ala Gly
                180                 185                 190

Leu Asn Phe Arg Ile Thr Tyr Ser Ile Val Gln Thr Asn Cys Ser Lys
                195                 200                 205

Glu Asn Phe Leu Phe Leu Thr Pro Asp Cys Lys Ser Leu Trp Asn Gly
            210                 215                 220

Asp Thr Gly Glu Cys Thr Asp Asn Ala Tyr Ile Asp Ile Gln Leu Arg
225                 230                 235                 240

Ile Ala Ser Phe Ser Gln Asn Cys Asp Ile Tyr Pro Gly Lys Asp Phe
                245                 250                 255

Val Gln Pro Pro Thr Lys Ile Cys Val Gly Cys Pro Arg Asp Ile Pro
                260                 265                 270

Thr Asn Ser Pro Glu Leu Glu Glu Thr Leu Thr His Thr Ile Thr Lys
            275                 280                 285

Leu Asn Ala Glu Asn Asn Ala Thr Phe Tyr Phe Lys Ile Asp Asn Val
290                 295                 300

Lys Lys Ala Arg Val Gln Val Ala Gly Lys Lys Tyr Phe Ile Asp
305                 310                 315                 320

Phe Val Ala Arg Glu Thr Thr Cys Ser Lys Glu Ser Asn Glu Glu Leu
                325                 330                 335

Thr Glu Ser Cys Glu Thr Lys Lys Leu Gly Gln Ser Leu Asp Cys Asn
                340                 345                 350

Ala Glu Val Tyr Val Val Pro Trp Glu Lys Lys Ile Tyr Pro Thr Val
                355                 360                 365

Asn Cys Gln Pro Leu Gly Met Ile Ser Leu Met Lys Arg Pro Pro Gly
            370                 375                 380

Phe Ser Pro Phe Arg Ser Arg Ile Gly Glu Ile Lys Glu Glu Thr
385                 390                 395                 400

Thr Val Ser Pro Pro His Thr Ser Met Ala Pro Ala Gln Asp Glu Glu
                405                 410                 415

Arg Asp Ser Gly Lys Glu Gln Gly His Thr Arg Arg His Asp Trp Gly
                420                 425                 430

His Glu Lys Gln Arg Lys His Asn Leu Gly His Gly His Lys His Glu
            435                 440                 445

Arg Asp Gln Gly His Gly His Gln Arg Gly His Gly Leu Gly His Gly
450                 455                 460

His Glu Gln Gln His Gly Leu Gly His Gly His Lys Phe Lys Leu Asp
465                 470                 475                 480

Asp Asp Leu Glu His Gln Gly Gly His Val Leu Asp His Gly His Lys
                485                 490                 495

His Lys His Gly His Gly His Gly Lys His Lys Asn Lys Gly Lys Lys
                500                 505                 510

Asn Gly Lys His Asn Gly Trp Lys Thr Glu His Leu Ala Ser Ser Ser
            515                 520                 525

Glu Asp Ser Thr Thr Pro Ser Ala Gln Thr Gln Glu Lys Thr Glu Gly
            530                 535                 540

Pro Thr Pro Ile Pro Ser Leu Ala Lys Pro Gly Val Thr Val Thr Phe
545                 550                 555                 560
```

```
Ser Asp Phe Gln Asp Ser Asp Leu Ile Ala Thr Met Met Pro Pro Ile
                565                 570                 575

Ser Pro Ala Pro Ile Gln Ser Asp Asp Trp Ile Pro Asp Ile Gln
            580                 585                 590

Ile Asp Pro Asn Gly Leu Ser Phe Asn Pro Ile Ser Asp Phe Pro Asp
        595                 600                 605

Thr Thr Ser Pro Lys Cys Pro Gly Arg Pro Trp Lys Ser Val Ser Glu
    610                 615                 620

Ile Asn Pro Thr Thr Gln Met Lys Glu Ser Tyr Tyr Phe Asp Leu Thr
625                 630                 635                 640

Asp Gly Leu Ser

<210> SEQ ID NO 12
<211> LENGTH: 427
<212> TYPE: PRT
<213> ORGANISM: Homo sapiens

<400> SEQUENCE: 12

Met Lys Leu Ile Thr Ile Leu Phe Leu Cys Ser Arg Leu Leu Leu Ser
1               5                   10                  15

Leu Thr Gln Glu Ser Gln Ser Glu Glu Ile Asp Cys Asn Asp Lys Asp
            20                  25                  30

Leu Phe Lys Ala Val Asp Ala Ala Leu Lys Lys Tyr Asn Ser Gln Asn
        35                  40                  45

Gln Ser Asn Asn Gln Phe Val Leu Tyr Arg Ile Thr Glu Ala Thr Lys
    50                  55                  60

Thr Val Gly Ser Asp Thr Phe Tyr Ser Phe Lys Tyr Glu Ile Lys Glu
65                  70                  75                  80

Gly Asp Cys Pro Val Gln Ser Gly Lys Thr Trp Gln Asp Cys Glu Tyr
                85                  90                  95

Lys Asp Ala Ala Lys Ala Ala Thr Gly Glu Cys Thr Ala Thr Val Gly
            100                 105                 110

Lys Arg Ser Ser Thr Lys Phe Ser Val Ala Thr Gln Thr Cys Gln Ile
        115                 120                 125

Thr Pro Ala Glu Gly Pro Val Val Thr Ala Gln Tyr Asp Cys Leu Gly
    130                 135                 140

Cys Val His Pro Ile Ser Thr Gln Ser Pro Asp Leu Glu Pro Ile Leu
145                 150                 155                 160

Arg His Gly Ile Gln Tyr Phe Asn Asn Asn Thr Gln His Ser Ser Leu
                165                 170                 175

Phe Met Leu Asn Glu Val Lys Arg Ala Gln Arg Gln Val Val Ala Gly
            180                 185                 190

Leu Asn Phe Arg Ile Thr Tyr Ser Ile Val Gln Thr Asn Cys Ser Lys
        195                 200                 205

Glu Asn Phe Leu Phe Leu Thr Pro Asp Cys Lys Ser Leu Trp Asn Gly
    210                 215                 220

Asp Thr Gly Glu Cys Thr Asp Asn Ala Tyr Ile Asp Ile Gln Leu Arg
225                 230                 235                 240

Ile Ala Ser Phe Ser Gln Asn Cys Asp Ile Tyr Pro Gly Lys Asp Phe
                245                 250                 255

Val Gln Pro Pro Thr Lys Ile Cys Val Gly Cys Pro Arg Asp Ile Pro
            260                 265                 270

Thr Asn Ser Pro Glu Leu Glu Glu Thr Leu Thr His Thr Ile Thr Lys
        275                 280                 285
```

```
Leu Asn Ala Glu Asn Ala Thr Phe Tyr Phe Lys Ile Asp Asn Val
        290                 295                 300

Lys Lys Ala Arg Val Gln Val Val Ala Gly Lys Lys Tyr Phe Ile Asp
305                 310                 315                 320

Phe Val Ala Arg Glu Thr Thr Cys Ser Lys Glu Ser Asn Glu Glu Leu
                325                 330                 335

Thr Glu Ser Cys Glu Thr Lys Lys Leu Gly Gln Ser Leu Asp Cys Asn
            340                 345                 350

Ala Glu Val Tyr Val Val Pro Trp Glu Lys Lys Ile Tyr Pro Thr Val
        355                 360                 365

Asn Cys Gln Pro Leu Gly Met Ile Ser Leu Met Lys Arg Pro Pro Gly
    370                 375                 380

Phe Ser Pro Phe Arg Ser Ser Arg Ile Gly Glu Ile Lys Glu Glu Thr
385                 390                 395                 400

Thr Ser His Leu Arg Ser Cys Glu Tyr Lys Gly Arg Pro Pro Lys Ala
                405                 410                 415

Gly Ala Glu Pro Ala Ser Glu Arg Glu Val Ser
            420                 425

<210> SEQ ID NO 13
<211> LENGTH: 362
<212> TYPE: PRT
<213> ORGANISM: Homo sapiens

<400> SEQUENCE: 13

Gln Glu Ser Gln Ser Glu Glu Ile Asp Cys Asn Asp Lys Asp Leu Phe
1               5                   10                  15

Lys Ala Val Asp Ala Ala Leu Lys Lys Tyr Asn Ser Gln Asn Gln Ser
            20                  25                  30

Asn Asn Gln Phe Val Leu Tyr Arg Ile Thr Glu Ala Thr Lys Thr Val
        35                  40                  45

Gly Ser Asp Thr Phe Tyr Ser Phe Lys Tyr Glu Ile Lys Glu Gly Asp
    50                  55                  60

Cys Pro Val Gln Ser Gly Lys Thr Trp Gln Asp Cys Glu Tyr Lys Asp
65                  70                  75                  80

Ala Ala Lys Ala Ala Thr Gly Glu Cys Thr Ala Thr Val Gly Lys Arg
                85                  90                  95

Ser Ser Thr Lys Phe Ser Val Ala Thr Gln Thr Cys Gln Ile Thr Pro
            100                 105                 110

Ala Glu Gly Pro Val Val Thr Ala Gln Tyr Asp Cys Leu Gly Cys Val
        115                 120                 125

His Pro Ile Ser Thr Gln Ser Pro Asp Leu Glu Pro Ile Leu Arg His
    130                 135                 140

Gly Ile Gln Tyr Phe Asn Asn Asn Thr Gln His Ser Ser Leu Phe Met
145                 150                 155                 160

Leu Asn Glu Val Lys Arg Ala Gln Arg Gln Val Val Ala Gly Leu Asn
                165                 170                 175

Phe Arg Ile Thr Tyr Ser Ile Val Gln Thr Asn Cys Ser Lys Glu Asn
            180                 185                 190

Phe Leu Phe Leu Thr Pro Asp Cys Lys Ser Leu Trp Asn Gly Asp Thr
        195                 200                 205

Gly Glu Cys Thr Asp Asn Ala Tyr Ile Asp Ile Gln Leu Arg Ile Ala
    210                 215                 220

Ser Phe Ser Gln Asn Cys Asp Ile Tyr Pro Gly Lys Asp Phe Val Gln
```

```
            225                 230                 235                 240

Pro Pro Thr Lys Ile Cys Val Gly Cys Pro Arg Asp Ile Pro Thr Asn
                    245                 250                 255

Ser Pro Glu Leu Glu Thr Leu Thr His Thr Ile Thr Lys Leu Asn
                    260                 265                 270

Ala Glu Asn Ala Thr Phe Tyr Phe Lys Ile Asp Asn Val Lys Lys
                    275                 280                 285

Ala Arg Val Gln Val Val Ala Gly Lys Lys Tyr Phe Ile Asp Phe Val
  290                 295                 300

Ala Arg Glu Thr Thr Cys Ser Lys Glu Ser Asn Glu Glu Leu Thr Glu
  305                 310                 315                 320

Ser Cys Glu Thr Lys Lys Leu Gly Gln Ser Leu Asp Cys Asn Ala Glu
                    325                 330                 335

Val Tyr Val Val Pro Trp Glu Lys Lys Ile Tyr Pro Thr Val Asn Cys
                    340                 345                 350

Gln Pro Leu Gly Met Ile Ser Leu Met Lys
                    355                 360

<210> SEQ ID NO 14
<211> LENGTH: 255
<212> TYPE: PRT
<213> ORGANISM: Homo sapiens

<400> SEQUENCE: 14

Ser Ser Arg Ile Gly Glu Ile Lys Glu Thr Thr Val Ser Pro Pro
  1                   5                   10                  15

His Thr Ser Met Ala Pro Ala Gln Asp Glu Arg Asp Ser Gly Lys
                    20                  25                  30

Glu Gln Gly His Thr Arg Arg His Asp Trp Gly His Glu Lys Gln Arg
                    35                  40                  45

Lys His Asn Leu Gly His Gly His Lys His Glu Arg Asp Gln Gly His
                    50                  55                  60

Gly His Gln Arg Gly His Gly Leu Gly His Gly Glu Gln Gln His
  65                  70                  75                  80

Gly Leu Gly His Gly His Lys Phe Lys Leu Asp Asp Asp Leu Glu His
                    85                  90                  95

Gln Gly Gly His Val Leu Asp His Gly His Lys His Lys His Gly His
                    100                 105                 110

Gly His Gly Lys His Lys Asn Lys Gly Lys Lys Asn Gly Lys His Asn
                    115                 120                 125

Gly Trp Lys Thr Glu His Leu Ala Ser Ser Ser Glu Asp Ser Thr Thr
                    130                 135                 140

Pro Ser Ala Gln Thr Gln Glu Lys Thr Glu Gly Pro Thr Pro Ile Pro
  145                 150                 155                 160

Ser Leu Ala Lys Pro Gly Val Thr Val Thr Phe Ser Asp Phe Gln Asp
                    165                 170                 175

Ser Asp Leu Ile Ala Thr Met Met Pro Ile Ser Pro Ala Pro Ile
                    180                 185                 190

Gln Ser Asp Asp Asp Trp Ile Pro Asp Ile Gln Ile Asp Pro Asn Gly
                    195                 200                 205

Leu Ser Phe Asn Pro Ile Ser Asp Phe Pro Asp Thr Thr Ser Pro Lys
                    210                 215                 220

Cys Pro Gly Arg Pro Trp Lys Ser Val Ser Glu Ile Asn Pro Thr Thr
  225                 230                 235                 240
```

```
Gln Met Lys Glu Ser Tyr Tyr Phe Asp Leu Thr Asp Gly Leu Ser
            245                 250                 255

<210> SEQ ID NO 15
<211> LENGTH: 207
<212> TYPE: PRT
<213> ORGANISM: Homo sapiens

<400> SEQUENCE: 15

Lys His Asn Leu Gly His Gly His Lys His Glu Arg Asp Gln Gly His
1               5                   10                  15

Gly His Gln Arg Gly His Gly Leu Gly His Gly His Glu Gln Gln His
            20                  25                  30

Gly Leu Gly His Gly His Lys Phe Lys Leu Asp Asp Asp Leu Glu His
        35                  40                  45

Gln Gly Gly His Val Leu Asp His Gly His Lys His Lys His Gly His
    50                  55                  60

Gly His Gly Lys His Lys Asn Lys Gly Lys Lys Asn Gly Lys His Asn
65                  70                  75                  80

Gly Trp Lys Thr Glu His Leu Ala Ser Ser Glu Asp Ser Thr Thr
                85                  90                  95

Pro Ser Ala Gln Thr Gln Glu Lys Thr Glu Gly Pro Thr Pro Ile Pro
            100                 105                 110

Ser Leu Ala Lys Pro Gly Val Thr Val Thr Phe Ser Asp Phe Gln Asp
        115                 120                 125

Ser Asp Leu Ile Ala Thr Met Met Pro Pro Ile Ser Pro Ala Pro Ile
    130                 135                 140

Gln Ser Asp Asp Asp Trp Ile Pro Asp Ile Gln Ile Asp Pro Asn Gly
145                 150                 155                 160

Leu Ser Phe Asn Pro Ile Ser Asp Phe Pro Asp Thr Thr Ser Pro Lys
                165                 170                 175

Cys Pro Gly Arg Pro Trp Lys Ser Val Ser Glu Ile Asn Pro Thr Thr
            180                 185                 190

Gln Met Lys Glu Ser Tyr Tyr Phe Asp Leu Thr Asp Gly Leu Ser
        195                 200                 205

<210> SEQ ID NO 16
<211> LENGTH: 58
<212> TYPE: PRT
<213> ORGANISM: Artificial Sequence
<220> FEATURE:
<223> OTHER INFORMATION: Synthetic Polypeptide

<400> SEQUENCE: 16

Met His Ser Phe Cys Ala Phe Lys Ala Asp Asp Gly Pro Cys Arg Ala
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 17
<211> LENGTH: 20
<212> TYPE: PRT
<213> ORGANISM: Artificial Sequence
<220> FEATURE:
<223> OTHER INFORMATION: Synthetic Polypeptide
```

<400> SEQUENCE: 17

Asp Trp Gly His Glu Lys Gln Arg Lys His Asn Leu Gly His Gly His
1               5                   10                  15

Lys His Glu Arg
            20

<210> SEQ ID NO 18
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 18

Lys Lys Ile Tyr Pro Thr Val Asn Cys Gln Pro Leu Gly Met Ile Ser
1               5                   10                  15

Leu Met Lys Arg Pro Pro Gly Phe Ser Pro Phe Arg Ser Ser Arg Ile
            20                  25                  30

Gly Glu

<210> SEQ ID NO 19
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 19

Ser Ser Arg Ile Gly Glu Ile Lys Glu
1               5

<210> SEQ ID NO 20
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 20

Lys Lys Ile Tyr Pro Thr Val Asn Cys Gln Pro Leu Gly Met Ile Ser
1               5                   10                  15

Leu Met Lys Arg Pro Pro Gly Phe Ser Pro Phe Arg Ser Ser Arg Ile
            20                  25                  30

Gly Glu

<210> SEQ ID NO 21
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 21

Lys Lys Ile Tyr Pro Thr Val Asn Cys Gln Pro Leu Gly Met Ile Ser
1               5                   10                  15

Leu Met Lys

<210> SEQ ID NO 22
<211> LENGTH: 7
<212> TYPE: PRT
<213> ORGANISM: Artificial Sequence
<220> FEATURE:

<223> OTHER INFORMATION: Synthetic Polypeptide

<400> SEQUENCE: 22

Ser Ser Arg Arg Ile Gly Glu
1               5

<210> SEQ ID NO 23
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 23

Lys Lys Tyr Ile Pro Thr Val Asn Cys Gln Pro Leu Gly Met Ile Ser
1               5                   10                  15

Leu Met Lys

<210> SEQ ID NO 24
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 24

Arg Pro Pro Gly Phe Ser Pro Phe Arg
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 25

Ser Ser Arg Ile Gly Glu Lys Glu
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 26

Ile Asn Pro Thr Thr Gln Met Lys Glu
1               5

<210> SEQ ID NO 27
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 27

Glu Asp Ser Thr Thr Pro Ser Ala Gln Thr Gln Glu
1               5                   10

<210> SEQ ID NO 28
<211> LENGTH: 11
<212> TYPE: PRT
<213> ORGANISM: Artificial Sequence

```
<220> FEATURE:
<223> OTHER INFORMATION: Synthetic Polypeptide

<400> SEQUENCE: 28

Tyr Lys Gly Arg Pro Pro Lys Ala Gly Ala Glu
1               5                   10

<210> SEQ ID NO 29
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 29

Ile Asn Pro Thr Gln Met Lys Glu
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 30

Ser Tyr Tyr Asp Asp Gly Leu Ser
1               5
```

PEPTIDE QUANTITATION ASSAY FOR DIFFERENTIATING FULL-LENGTH HIGH MOLECULAR WEIGHT KININOGEN (HMWK) AND CLEAVED HMWK

CROSS REFERENCE TO RELATED APPLICATIONS

This application is a national stage filing under 35 U.S.C. § 371 of International Patent Application Serial No. PCT/US2016/066936, filed Dec. 15, 2016, entitled "PEPTIDE QUANTIFICATION ASSAY FOR DIFFERENTIATING FULL-LENGTH HIGH MOLECULAR WEIGHT KININOGEN (HMWK) AND CLEAVED HMWK," which claims the benefit of the filing date of U.S. Provisional Application Ser. No. 62/267,734, filed Dec. 15, 2015, under 35 U.S.C. § 119, the entire contents of each of which are incorporated by reference herein.

BACKGROUND OF THE INVENTION

Kininogens are precursors of kinin, such as bradykinin and kallidin. There are two types of human kininogens, high molecular-weight kininogen (HMWK) and low molecular-weight kininogen (LMWK), which are splicing variants. HMWK acts mainly as a cofactor on coagulation and inflammation and is the preferred substrate for plasma kallikrein (pKal)-mediated bradykinin generation. Both HMWKs and LMWKs are cysteine protease inhibitors.

HMWK is a circulating plasma protein, which participates in the initiation of blood coagulation. HMWK also generates the vasodilator bradykinin via the Kallikrein-kinin system. HMWK adheres to cell surface receptors on the endothelium, monocytes, and platelets, thereby localizing coagulation and bradykinin generation. The active peptide bradykinin that is released from HMWK shows a variety of physiological effects. Like smooth muscle contraction, hypotension, diuresis, decrease in blood glucose level, it is a mediator of inflammation and has a cardio protective effect, directly via bradykinin action, indirectly via endothelium-derived relaxing factor action. Bradykinin is a key mediator of pain, inflammation, edema and angiogenesis.

Plasma kallikrein (pKal) is the primary bradykinin-generating enzyme in the circulation. The activation of pKal occurs via the contact system, which has been linked to disease pathology associated with hereditary angioedema (HAE). pKal cleaves HMWK (a single-chain polypeptide) to produce bradykinin and a cleaved form HMWK, which contains two polypeptide chains (a heavy chain and a light chain) held together by a disulfide bond. Cugno et al., Blood (1997) 89:3213-3218. The light chain in the initial cleaved HMWK is around 56 kDa and would further be cleaved to form a 46 kDa shorter form.

Cleaved HMWK increased to about 47% of total kininogen during a hereditary angioedema (HAE) attack, making it a biomarker for monitoring HAE attack. Cugno et al., 1997. It is therefore of interest to develop sensitive and reliable assays for detecting the level of cleaved HMWK in biological samples.

SUMMARY OF THE INVENTION

The present disclosure is based, at least in part, on the development of sensitive and selective assay methods, which may involve liquid chromatography-mass spectrometry (LC-MS) using, e.g., multiple reaction monitoring (MRM) for differentiating full-length HMWK and cleaved HMWK. Such assay methods utilize signature peptides which are indicative of cleaved HMWK (e.g., C-terminal peptides from the heavy chain or N-terminal peptides from the light chains), and/or full-length HMWK (e.g., as relative to low molecular weight kininogen).

Accordingly, one aspect of the present disclosure provides a method for detecting cleaved high molecular weight kininogen (HMWK) in a sample, the method comprising: (i) providing a sample suspected of containing HMWK, (ii) contacting the sample with a protease to generate a plurality of digested peptides; and (iii) measuring the level of a signature peptide in the plurality of digested peptides, wherein the signature peptide is indicative of cleaved HMWK.

In some embodiments, the signature peptide is indicative of the 46 kDa light chain of cleaved HMWK, including, but not limited to: KHNLGHGH (SEQ ID NO: 1), KHNLGHGHKHE (SEQ ID NO: 2); KHNLGHGHK (SEQ ID NO: 3); or KHNLGHGHKHER (SEQ ID NO: 4).

In some embodiments, the signature peptide is indicative of the 56 kDa light chain of cleaved HMWK, e.g., SSRIGE (SEQ ID NO: 5).

The method described herein may further comprise measuring the level of a signature peptide that is indicative of full-length HMWK, including, but not limited to: GHEKQRKH (SEQ ID NO: 6); KQRKHNLGHGHKHE (SEQ ID NO: 7); DWGHKQRKHNLGHGHKHER (SEQ ID NO: 8); HNLGHGHK (SEQ ID NO: 9); or SYYFDLTDGLS (SEQ ID NO: 10).

In another aspect, the present disclosure features a method for differentiating full-length high molecular weight kininogen (HMWK) and cleaved HMWK in a sample. The method comprise: (i) providing a sample suspected of containing full-length HMWK and/or cleaved HMWK; (ii) contacting the sample with a protease to generate a plurality of digested peptides; (iii) measuring the level of a first digested peptide (e.g., SSRIGE; SEQ ID NO: 5) obtained from step (ii), wherein the first digested peptide is unique to cleaved HMWK as compared with full-length HMWK (e.g., a signature peptide for cleaved HMWK); (iv) measuring the level of a second digested peptide obtained from step (ii), wherein the second digested peptide (e.g., SYYFDLTDGLS; SEQ ID NO: 10) is unique to HMWK as compared with low molecular weight kininogen (LMWK) (e.g., a signature peptide for HMWK); (v) determining the ratio between the first digested peptide and the second digested peptide; and (vi) differentiating cleaved HMWK from full-length HMWK in the sample based on the ratio determined in step (v).

In any of the assay methods described herein, the protease for use in digesting HMWK in a sample may be endoproteinase chymotrypsin, endoproteinase Glu-C, endoproteinase Asp-N, cathepsin G, or endoproteinase Lys-C. In some embodiments, any of the signature peptides can be measured by liquid chromatograph-mass spectrometry (LC-MS), e.g., MRM-MS.

A sample to be analyzed by any of the assay methods described herein can be a biological sample (e.g., a blood sample or a plasma sample or a serum sample) obtained from a human subject, e.g., a human patient having or suspected of having hereditary angioedema (HAE). In some examples, the biological sample can be a normal plasma sample, a plasma sample activated by FXIIa, or a non-activated plasma sample. When the biological sample is a plasma sample, it can be collected in an evacuated blood collection tube (e.g., a sample collection anticoagulant tube, "SCAT tube"), which comprises a liquid formulation that comprises a mixture of protease inhibitors.

In some embodiments, the protease digestion step of any of the assay methods described herein may be performed in the presence of a reducing agent, e.g., DTT, BME, or TCEP. For example, the biological sample may be incubated with the reducing agent at 90° C. for 1 hour. In some examples, the protease digestion step may be performed in the absence of a protease inhibitor, an anticoagulant (e.g., citrate), or both. In some examples, the ratio of protease/protein is about 1:20, e.g., Glu C/protein is 1:20.

Any of the assay methods may be applied for HAE diagnosis and/or prognosis. Accordingly, the present disclosure also provides methods for identifying human subjects who have HAE or is an HAE patient at risk for an HAE attack. In some embodiments, the level of cleaved HMWK (e.g., the heavy chain-light chain dimer, the heavy chain, or the light chain such as the 46 kDa light chain or the 56 kDa light chain) determined by an assay method described herein can be relied on for determining whether a human subject has HAE or is at risk for an HAE attack, wherein an elevated level of cleaved HMWK is indicative of HAE or risk for HAE attack. In other embodiments, the ratio between a signature peptide of cleaved HMWK and a signature peptide of HMWK determined by an assay method described herein is relied on for determining whether a human subject has HAE or is at risk for HAE attack, wherein an elevated level of such a ratio is indicative of HAE or HAE attack.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

FIG. 2 is a diagram showing peptides generated by Glu C digestion at 25° C. and 37° C. of HMWK standards, which were obtained from Sigma (HK_Sigma) or Enzyme Research (HK_Enzyme Research). This figure depicts SEQ ID NOs: 5, 19, 24, 30, 29, and 7 from top to bottom, respectively.

DETAILED DESCRIPTION OF THE INVENTION

Figure 1:
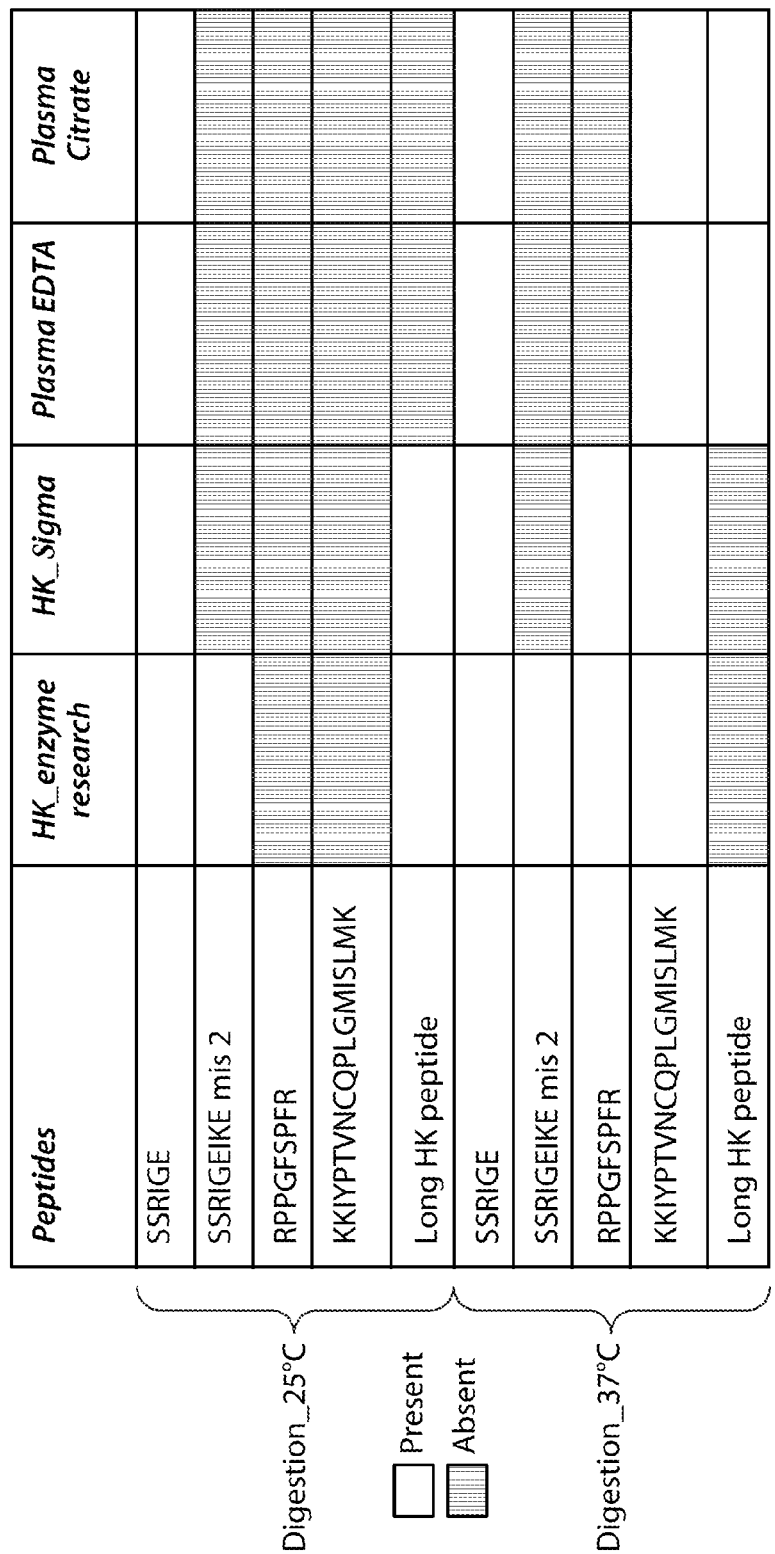
FIG. 1 is a diagram showing exemplary peptides obtained from enzyme digestion of cleaved HMWK (e.g., the 56 kDa light chain) found in plasma and commercially available HMWK (HK) samples at optimal temperatures by MRM analysis. This figure depicts SEQ ID NOs: 5, 19, 24, and 21 repeated from top to bottom, respectively.

Plasma kallikrein (PKal) is a serine protease component of the contact system and is the primary bradykinin-generating enzyme in the circulation. The contact system is activated by either factor XIIa (the active form of Factor XII or FXII) upon exposure to foreign or negatively charged surfaces or on endothelial cell surfaces by prolylcarboxypeptidases (Sainz I. M. et al., Thromb Haemost 98, 77-83, 2007). Activation of the plasma kallikrein amplifies intrinsic coagulation via its feedback activation of factor XII and proteolytically cleaves the kininogen precursor, high molecular weight kininogen (HMWK), releasing the proinflammatory nonapeptide bradykinin and a cleaved HMWK, which contains two polypeptide chains linked by a disulfide bond (also known as 2-chain HMWK).

As the primary kininogenase in the circulation, plasma kallikrein is largely responsible for the generation of bradykinin in the vasculature. A genetic deficiency in the C1-inhibitor protein (C1-INH) leads to hereditary angioedema (HAE). Patients with HAE suffer from acute attacks of painful edema often precipitated by unknown triggers (Zuraw B. L. et al., N Engl J Med 359, 1027-1036, 2008). Through the use of pharmacological agents or genetic studies in animal models, the plasma kallikrein-kinin system (plasma KKS) has been implicated in various diseases.

High molecular-weight kininogen (HMWK) exists in the plasma as a single polypeptide (1-chain) multi-domain (domains 1-6) protein with a molecular weight of approximately 110 kDa. HMWK can be cleaved by pKal within domain 4 to release the 9 amino acid, pro-inflammatory peptide bradykinin and a 2-chain form of HMWK (cleaved kininogen). The two chains of HMWK are the heavy chain, which contains the domains 1-3 of HMWK, and the light chain, which contains the domains 5 and 6 of HMWK. The heavy chain has a molecular weight of approximately 65 kDa whereas the light chain exists as two species with molecular weights of approximately 56 and 46 kDa.

The level of cleaved HMWK (e.g., 2-chain HMWK) was found to be elevated in HAE attack, as well as in other pKal-associated disorders. Thus, cleaved HMWK can serve as a biomarker for monitoring disease development and/or treatment efficacy. However, the art lacks suitable agents and/or suitable assays that can effectively distinguish intact HMWK from its cleaved version.

The present disclosure is based, at least in part, on the discovery of signature peptides indicative of the cleaved HMWK, for example, the light chain (e.g., the 46 kDa light chain) of the 2-chain HMWK and signature peptides indicative of HMWK (e.g., the full-length HMWK). Unless otherwise specified, the term "cleaved HMWK" refers to the 2-chain dimer described herein, the heavy chain of the dimer, or the light chain of the dimer (including the 56 kDa light chain and the 46 kDa light chain). Based on the discovery of such signature peptides, sensitive and selective assay methods were developed for measuring cleaved HMWK as relative to HMWK. The assay methods described herein may be used for both clinical applications, e.g., diagnosis or prognosis of HAE, and non-clinical applications, for example, for research and preclinical drug development purposes.

I. Methods for Measuring Cleaved HMWK

In some aspects, described herein are methods for measuring cleaved HMWK in a sample, e.g., differentiating cleaved HMWK from full-length HMWK in a sample. Such a method may involve treating a suitable sample suspected of containing full-length HMWK, cleaved HMWK or both with a suitable protease to generate a plurality of digested peptides and measuring the levels of one or more signature peptides indicative of cleaved HMWK and/or full-length HMWK. Either the level of cleaved HMWK or a ratio between cleaved HMWK and full-length HMWK can be used to indicate the pKal activity in the sample, which correlates with HAE or a risk of HAE attack.

(i) Full-Length HMWK and Cleaved HMWK

The human gene encoding HMWK is kininogen 1 (KNG1). KNG1 is transcribed and alternatively spliced to form mRNAs that encode either HMWK or low molecular weight kininogen (LMWK). Exemplary protein sequences of human HMWK and LMWK are provided below (the region of bradykinin is highlighted and in boldface):

```
>gi|56231037|ref|NP_001095886.1|kininogen-1 isoform 1 precursor [Homo
sapiens]
                                                   (SEQ ID NO: 11)

MKLITILFLC SRLLLSLTQE SQSEEIDCND KDLFKAVDAA LKKYNSQNQS NNQFVLYRIT

EATKTVGSDT FYSFKYEIKE GDCPVQSGKT WQDCEYKDAA KAATGECTAT VGKRSSTKFS

VATQTCQITP AEGPVVTAQY DCLGCVHPIS TQSPDLEPIL RHGIQYFNNN TQHSSLFMLN

EVKRAQRQVV AGLNFRITYS IVQTNCSKEN FLFLTPDCKS LWNGDTGECT DNAYIDIQLR

IASFSQNCDI YPGKDEVQPP TKICVGCPRD IPTNSPELEE TLTHTITKLN AENNATFYFK

IDNVKKARVQ VVAGKKYFID FVARETTCSK ESNEELTESC ETKKLGQSLD CNAEVYVVPW

EKKIYPTVNC QPLGMISLMK RPPGFSPFRS SRIGEIKEET TVSPPHTSMA PAQDEERDSG

KEQGHTRRHD WGHEKQRKHN LGHGHKHERD QGHGHQRGHG LGHGHEQQHG LGHGHKFKLD

DDLEHQGGHV LDHGHKHKHG HGHGKHKNKG KKNGKHNGWK TEHLASSSED STTPSAQTQE

KTEGPTPIPS LAKPGVTVTF SDFQDSDLIA TMMPPISPAP IQSDDDRUPD IQIDPNGLSF

NPISDFPDTT SPKCPGRPWK SVSEINPTTQ MKESYYFDLT DGLS

>gi|4504893|ref|NP_000884|kininogen-1 isoform 2 precursor [Homo sapiens]
                                                   (SEQ ID NO: 12)
mklitilflc srlllsltqe sqseeidcnd kdlfkavdaa lkkynsqnqs nnqfvlyrit eatktvgsdt fysfkyeike gdcpvqsgkt wqdceykdaa kaatgectat vgkrsstkfs vatqtcqitp aegpvvtaqy dclgcvhpis tqspdlepil rhgiqyfnnn tqhsslfmln evkraqrqvv aglnfritys ivqtncsken flfltpdcks lwngdtgect dnayidiqlr iasfsqncdi ypgkdfvqpp tkicvgcprd iptnspelee tlthtitkln aennatfyfk idnvkkarvq vvagkkyfid fvarettcsk esneeltesc etkklgqsld cnaevyvvpw ekkiyptvnc qplgmislmk rppgfspfrs srigeikeet tshlrsceyk grppkagaep aserevs
```

Exemplary sequences of the heavy and light chains of cleaved kininogen are provided below.

```
>cleaved kininogen-1 heavy chain (italicized
region in SEQ ID NO: 11 above)
                                                   (SEQ ID NO: 13)
QESQSEEIDC NDKDLFKAVD AALKKYNSQN QSNNQFVLYR

ITEATKTVGS DTFYSFKYEI KEGDCPVQSG KTWQDCEYKD

AAKAATGECT ATVGKRSSTK FSVATQTCQI TPAEGPVVTA

QYDCLGCVHP ISTQSPDLEP ILRHGIQYFN NNTQHSSLFM

LNEVKRAQRQ VVAGLNFRIT YSIVQTNCSK ENFLFLTPDC

KSLWNGDTGE CTDNAYIDIQ LRIASFSQNC DIYPGKDFVQ

PPTKICVGCP RDIPTNSPEL EETLTHTITK LNAENNATFY
```

```
FKIDNVKKAR VQVVAGKKYF IDFVARETTC SKESNEELTE

SCETKKLGQS LDCNAEVYVV PWEKKIYPTV NCQPLGMISL MK

>cleaved kininogen-1 light chain (56 kDa)
(boldfaced region in SEQ ID NO: 11 above)
                                                   (SEQ ID NO: 14)
SSRIGEIKEE TTVSPPHTSM APAQDEERDS GKEQGHTRRH

DWGHEKQRKH NLGHGHKHER DQGHGHQRGH GLGHGHEQQH

GLGHGHKFKL DDDLEHQGGH VLDHGHKHKH GHGHGKHKNK

GKKNGKHNGW KTEHLASSSE DSTTPSAQTQ EKTEGPTPIP

SLAKPGVTVT FSDFQDSDLI ATMMPPISPA PIQSDDDWIP

DIQIDPNGLS FNPISDFPDT TSPKCPGRPW KSVSEINPTT

QMKESYYFDL TDGLS

>cleaved kininogen-1 light chain (46 KD)
(italicized and boldfaced region in SEQ ID
No: 11 above)
                                                   (SEQ ID NO: 15)
KHNLGHGHKH ERDQGHGHQR GHGLGHGHEQ QHGLGHGHKF

KLDDDLEHQG GHVLDHGHKH KHGHGHGKHK NKGKKNGKHN

GWKTEHLASS SEDSTTPSAQ TQEKTEGPTP IPSLAKPGVT
```

-continued

```
VTFSDFQDSD LIATMMPPIS PAPIQSDDDW IPDIQIDPNG

LSFNPISDFP DTTSPKCPGR PWKSVSEINP TTQMKESYYF

DLTDGLS
```

(ii) Sample Preparation

Any sample that may contain HMWK (e.g., full-length HMWK, cleaved HMWK, or both) can be analyzed by the method described herein. As used herein, a "sample" refers to a composition that may comprise an analyte of interest (HMWK in the present case). A sample may comprise tissue, e.g., blood, plasma or protein, from a subject. A sample can include both an initial unprocessed sample taken from a subject as well as subsequently processed, e.g., partially purified or preserved forms, for example, via immunoprecipitation. Exemplary samples include blood, plasma, serum, tears, or mucus. In other examples, a sample may be a composition of an in vitro assay.

In some embodiments, the sample is a body fluid sample such as a serum or plasma sample. Such a sample may be a biological sample obtained from a subject in need of the analysis. A "patient," "subject" or "host" (these terms are used interchangeably) to be treated by the subject method may mean either a human or non-human animal. In some instances, the subject is a human patient, who may have, be suspected of having, or at risk for a disease associated with the contact system. For example, the human patient may have prior occurrence of HAE or may be at risk for HAE. Such a human patient may be treated previously or is in the course of treatment with a drug that targets a component of the contact system (e.g., pKal or FXIIa or high molecular weight kininogen).

The biological sample may be a body fluid sample, e.g., a blood sample or plasma sample. The plasma sample for use in the method described herein may be collected and processed in an evacuated blood collection tube (e.g., a sample collection anticoagulant tube or SCAT tube), which is commonly used in medical practices for collecting blood samples for various uses. The tubes described herein may be non-glass tubes comprising a liquid formulation that comprises a mixture of protease inhibitors (a protease inhibitor cocktail).

In some embodiments, the protease inhibitor cocktail may comprise at least one serine proteinase inhibitor and at least one cysteine proteinase inhibitor. At least one serine proteinase inhibitor can be a plasma kallikrein inhibitor. Such proteinase inhibitor cocktails may comprise multiple (e.g., 2, 3, 4, or 5) serine protease inhibitors, at least one of which can be a trypsin or human plasmin inhibitor. Preferably, the proteinase inhibitor cocktails described herein are substantially free of a protease inhibitor that is unstable in an aqueous solution, i.e., the activity of the protease inhibitor that is unstable in an aqueous solution is insubstantial as relative to the total inhibitory activity of the protease cocktail. In some instances, the amount of the protease inhibitor that is unstable in an aqueous solution may be less than 5% (w/w) of the total protease inhibitors in the cocktail, e.g., less than 2%, less than 1%, or less than 0.5%. In some instances, the protease inhibitor cocktail is completely free of a protease inhibitor that is unstable in an aqueous solution (e.g., an aqueous solution having a pH of 4-6). One example of protease inhibitor that is not stable in an aqueous solution is PPACK II, also known as H-D-Phe-Phe-Arg-chloromethyl ketone.

Exemplary serine protease inhibitors, cysteine protease inhibitors, and trypsin protease inhibitors are listed in the table below, which can be used for making the protease inhibitor cocktails described herein.

| Categories | Exemplary Inhibitors |
|---|---|
| Serine Proteinase Inhibitors | Benzamidine<br>4-(2-Aminoethyl) benzenesulfonyl fluoride hydrochloride (AEBSF);<br>Chymostatin;<br>Nalpha-Tosyl-Lys Chloromethyl Ketone (TLCK);<br>Tos-Phe-CH2Cl; N-p-Tosyl-L-phenylalanine chloromethyl ketone (TPCK)<br>1-({(6R,7S)-3-Racetyloxy)methyl{-7-methoxy-5,5-dioxido-8-oxo-5-thia-1-azabicyclo[4.2.0]oct-2-en-2-yl}carbonyl)-L-proline<br>Patamostat mesylate;<br>Gabexate mesylate;<br>Msaapvck (Meosuc-aapv-cmk; MeOSuc-Ala-Ala-Pro-Val-CMK)<br>Nafamostat mesylate;<br>Rosmarinic acid;<br>Purpurogallin;<br>2-(4-((1-Acetimidoyl-3-pyrrolidinyl)oxy)phenyl)-3-(7-amidino-2-naphthyl)propanoic acid hydrocloride pentahydrate<br>4-(4-Bromophenylsulfonylcarbamoyl)benzoyl-L-valyl-L-proline-1(RS)-(1-trifluoroacetyl-2-methylprolyl)amide<br>L-658758; CHEMBL446371; L 658758<br>Sivelestat;<br>Patamostat;<br>Cholesterol sulfate;<br>Elastase Inhibitor III;<br>Gabexate;<br>4',6-Diamidino-2-phenylindole;<br>4-aminobenzamidine;<br>3,4-dichloroisocoumarin;<br>Bivalirudin Trifluoroacetate<br>Pradaxa;<br>HIRUDIN;<br>Ximelagatran;<br>Lepirudin; Refludan; Hbw 023<br>Bivalirudin;<br>Letaxaban;<br>Eribaxaban;<br>Dabigatran etexilate mesylate;<br>Apixaban;<br>Tanexaban;<br>Rivaroxaban; Xarelto; 366789-02-8<br>Plasma kallikrein inhibitors such as EPL-KAL2, DX-88, DX-2930, etc.<br>The following examples are trypsin and/or human plasmin inhibitors:<br>Soybean trypsin inhibitor<br>4-(2-aminoethyl)benzenesulfonylfluoride<br>4-aminobenzamidine<br>alpha 1-Antitrypsin<br>Aprotinin<br>Camostat<br>Eco protein (*E coli*)<br>inter-alpha-inhibitor<br>Nafamostat<br>NCO 650<br>Ovomucin<br>Somatomedin B<br>Trypsin Inhibitor (Bowman-Birk Soybean)<br>Trypsin Inhibitor (Kunitz Soybean)<br>Urinastatin |
| Cysteine Proteinase Inhibitor | Geldanamycin; 30562-34-6; AKOS022185390<br>Calpastatin;<br>L-Proline,N4R25,35)-3-[(propylamino)carbonyl]-2-oxiranyl]carbonyl]-L-isoleucyl-;<br>Proteasome Inhibitor I;<br>(L-3-trans-(Propylcarbamyl)oxirane-2-carbonyl)-L-isoleucyl-L-proline;<br>Calpain Inhibitor III;<br>[L-3-trans-(Propylcarbamoyl)oxirane-2-carbonyl]-L-isoleucyl-L-proline;<br>Omuralide; |

| Categories | Exemplary Inhibitors |
|---|---|
| | (S)-MG132;<br>Lactacystin;<br>Z-Phe-ala-diazomethane;<br>Leupeptin;<br>4-Hydroxynonenal;<br>trans-Epoxysuccinyl-L-leucylamido(4-guanidino)butane;<br>Loxistatin;<br>Clasto-lactacystinbeta-lactone;<br>L-Proline,<br>Z-FA-FMK;<br>N-acetylleucyl-leucyl-methioninal;<br>nitroaspirin;<br>Allnal;<br>Aloxistatin;<br>ethyl 3-(14-methyl- 14(3 -methylbutyl)amino]-1-<br>oxopentan-2-yl}carbamoyl)oxirane-2-carboxylate ;<br>(+/−)4-HYDROXYNON-2-ENAL; |

In some examples, the protease inhibitor cocktail contained in the evacuated blood collection tubes comprises at least one serine proteinase inhibitor (e.g., 1, 2, or 3), which may include at least one trypsin/plasmin inhibitor (e.g., 1, 2, or 3), and at least one cysteine protease inhibitor (e.g., 1, 2, or 3). Such a protease inhibitor cocktail may comprise three serine proteinase inhibitors (e.g., benzamidine, AEBSF, and a trypsin/plasmin inhibitor such as soybean trypsin inhibition) and one cysteine protease inhibitor (e.g., leupeptin).

In other examples, the protease inhibitor cocktail may comprise at least one serine protease inhibitor (e.g., a plasma kallikrein inhibitor) and at least one cysteine protease inhibitor (e.g., leupeptin). The plasma kallikrein inhibitor may be EPI-KAL2 (Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ser Tyr Gly Gly Cys Gly Gly Asn Gln Asn Arg Phe Glu Ser Leu Glu Glu Cys Lys Lys Met Cys Thr Arg Asp; SEQ ID NO: 16), which is a specific plasma kallikrein, recombinant protease inhibitor that offers the ability for the tubes to contain a reagent that permits detection of activated plasma kallikrein using, e.g., immunoassays.

Any of the protease inhibitor cocktails may be dissolved in a suitable solution to form a liquid formulation. The suitable solution may be an acid-citrate-dextrose solution, which may comprise trisodium citrate, citric acid, and dextrose. The solution may have a pH value of about 4-6, e.g., 4.5. The liquid formulation may further comprise a cationic polymer such as hexadimethrine bromide molecule (Polybrene®), which can reduce contact system activation by interaction with negatively charged surfaces and a chelating agent (e.g., EDTA), which can inhibit metalloproteases.

The concentration of each of the protease inhibitors in the cocktail may be 5× or 10× higher than the final concentration of such an inhibitor for use in inhibiting the corresponding protease, depending upon the dilution fold in practice. The final concentration of a specific commercially protease inhibitor was known in the art and can be obtained from manufacturer's protocol. In some examples, the concentration of EPI-KAL2 may range from 5-15 µM (e.g., 5-10 or 10-15 µM), the concentration of leupeptin may range from 200-300 µM (e.g., 200-250, 240-270, or 250-300 µM); the concentration of soybean trypsin inhibitor may range from 1-3 mg/ml (e.g., 1-2 or 2-3 mg/ml); the concentration of benzamidine can range from 80-120 mM (e.g., 80-100 or 100-120 mM); and/or the concentration of AEBSF may range from 10-30 mM (e.g., 10-20 or 20-30 mM).

When a peptide-based protease inhibitor (e.g., EPI-KAL2) is used, it may be biotinylated following conventional methodology. For example, the peptide inhibitor may be biotinylated as follows. Briefly, the peptide inhibitor can be dissolved in a suitable solution, such as phosphate-buffered saline (PBS). Freshly prepared Sulfo-NHS-LC-Biotin can be added to the peptide inhibitor solution and incubated on ice for a suitable period of time. Excess non-reacted and hydrolyzed biotin can be removed using a spin-desalting column. The labeling of the peptide inhibitor can be confirmed by ELISA and the protein concentration can be determined by the Bradford assay.

Any of the liquid formulations described herein can be prepared by routine methods, e.g., dissolving the proper components into a suitable solution, and placed in evacuated blood collection tubes, which preferably is non-glass. The tubes may be stored at −20° C. and may be thawed on ice or in a refrigerator within a suitable period of time prior to use.

In specific examples, the evacuated blood collection tubes used in the methods described herein are SCAT tubes, including SCAT 169 and SCAT 153 as detailed below:

SCAT169: Evacuated 5 mL total volume plastic tubes containing (0.5 ml): 100 mM benzamidine, 400 µg/mL Polybrene®, 2 mg/mL soybean trypsin inhibitor, 20 mM EDTA, 263 µM leupeptin, and 20 mM AEBSF (4-(2-Aminoethyl) benzenesulfonyl fluoride hydrochloride) dissolved in acid-citrate-dextrose (100 mM trisodium citrate, 67 mM citric acid, and 2% dextrose, pH 4.5).

SCAT153: Evacuated 5 ml total volume plastic tubes containing (0.5 ml):10 µM biotinylated EPI-KAL2, 400 µg/mL Polybrene®, 20 mM EDTA, and 263 µM leupeptin, dissolved in acid-citrate-dextrose (100 mM trisodium citrate, 67 mM citric acid, and 2% dextrose, pH 4.5).

After blood collection, the blood samples may be processed to produce plasma samples within a suitable period of time (e.g., not exceeding an hour). The plasma samples can be subject to further analysis to assess features associated with the contact system of the subject from whom the initial blood sample is obtained.

(iii) Protease Digestion

The biological sample described herein, e.g., whole plasma sample as prepared following the processes described herein, may be treated with a suitable protease to generate a plurality of digested peptides. Alternatively, HMWK proteins, including both full-length and cleaved forms, may be enriched from the sample via, e.g., immunoprecipitation or denatured by methanol crash, prior to protease digestion.

Any suitable protease can be used in the method described herein. Preferably the protease cleaves a protein at a specific motif/residue such that the digested peptides can be identified based on the amino acid sequence of the protein. In some examples, the protease used in the methods cleaves after a glutamic acid residue. Exemplary proteases include, but are not limited to, endoproteinase Glu-C or cathepsin G. In other examples, the protease used in the assay methods described herein cleaves before an aspartic acid residue, e.g., endonuclease Asp-N, or after a lysine residue, e.g., endonuclease Lys-C. In another example, the protease used in the assay methods described herein cleaves after an amino acid residue carrying a large hydrophobic side chain (e.g., tyrosine, tryptophan, or phenylalanine). One example of such proteases is chymotrypsin.

The protease cleavage reaction can be performed under suitable conditions allowing for complete digestion of full-length and cleaved HMWK proteins in the sample. In some embodiments, the protease cleavage reaction mixture may contain a reducing agent, such as dithiothreitol (DTT), b-mercaptoethanol (BME), or tris(2-carboxyethyl)phosphine (TCEP), at a suitable concentration (e.g., 1 mM, 0.5 mM, 0.1 mM, or 0.05 mM). For example, when DTT is used, its concentration can be 0.1 mM or 0.05 mM. The protease cleavage reaction may be performed at a suitable temperature (e.g., 25° C., 37° C., 50° C., 55° C., or 90° C.) for a suitable period (e.g., 30 min, 60 min, ~90 min or 180 min).

In some examples, the mixture containing the reducing agent can be incubated at a high temperature for a suitable period of time (e.g., 55° C. for 30' or 60', or 90° C. for 30' or 60') to allow for complete denaturation of the proteins in the sample. The protease can then be added into the mixture and the digestion reaction can be carried out under a suitable temperature for a suitable period of time. The exact digestion temperature/time would depend on the specific protease used in the method, which is within the knowledge of a skilled person in the art. In one example, a Glu C enzyme is used and the digestion reaction can be carried out at 25° C. or 37° C. overnight (e.g., 12 hours, 14 hours, 17 hours, or 19 hours). In another example, chymotrypsin is used and the digestion reaction can be carried out at 40-60° C. (e.g., 50° C.) for a suitable period, for example, 2-5 hours (e.g., 3 hours).

chain, of cleaved HMWK) refers to a peptide that can only be generated from protease digestion of the cleaved HMWK (e.g., the heavy chain or the light chain of the cleaved HMWK) and cannot be generated by digestion of the full-length HMWK by the same protease. Similarly, a signature peptide of full-length HMWK is a peptide that can only be generated by protease digestion of the one-chain HMWK, but cannot be generated by digestion of the cleaved HMWK using the same protease. A signature peptide of HMWK refers to a peptide that is generated by protease digestion of HMWK (one-chain HMWK, two-chain HMWK, or both) but cannot be generated by digestion of LMWK using the same protease.

Exemplary signature peptides for cleaved HMWK includes (a) signature peptides for the 56 kDa light chain, e.g., SSRIGE (SEQ ID NO: 5), which may be produced by Glu-C digestion, and (b) signature peptides for the 46 kDa light chain, e.g., KHNLGHGH (SEQ ID NO: 1), KHNLGHGHKHE (SEQ ID NO: 2); KHNLGHGHKHER (SEQ ID NO: 4), or KHNLGHGHK (SEQ ID NO: 3), which may be generated by chymotrypsin digestion, Glu-C digestion, Asp-N digestion, and Lys-C digestion, respectively.

Table 1 below lists exemplary signature peptides for the 46 kDa light chain of cleaved HMWK produced by different proteases:

TABLE 1

Signature peptides derived from digestion of HMWK with various enzymes

| Enzyme | 46 K light chain peptide | HMWK peptide |
| --- | --- | --- |
| Chymotrypsin | KHNLGHGH (SEQ ID NO: 1) | GHEKQRKH (SEQ ID NO: 6) |
| Glu-C | KHNLGHGHKHE (SEQ ID NO: 2) | KQRKHNLGHGHKHE (SEQ ID NO: 7) |
| Asp-N | KHNLGHGHKHER (SEQ ID NO: 4) | DWGHEKQRKHNLGHGHKHER (SEQ ID NO: 17) |
| Lys-C | KHNLGHGHK (SEQ ID NO: 3) | HNLGHGHK (SEQ ID NO: 9) |

The reaction mixture may be free of protease inhibitors, anticoagulant such as citrate or both. The enzyme/protein ratio in the reaction may range from 1:5-1:30, for example, 1:5, 1:10, 1:20, 1:25, or 1:30. Selection of specific reaction conditions, including temperature, reaction time period, enzyme/protein ratio, presence/absence of protease inhibitor, presence/absence of anticoagulant, and presence/absence of reducing agents, may depend on the type of protease used and the sample to be treated, which can be determined via methods known in the art or those described herein.

(iv) Measurement of Signature Peptides

Signature peptides refer to digested peptides generated from the protease reactions and are unique to one type of kininogen as compared with another type of kininogen. Such peptides can be identified based on the specificity of the protease used in the method described herein and the amino acid sequences of different types of kininogens. See, e.g., disclosures herein. A peptide (signature peptide) unique to a first type of kininogen (e.g., full-length kininogen) as relative to a second type of kininogen (e.g., cleaved kininogen) refers to a peptide that can only be generated by cleaving the first type of kininogen using a protease but not by cleaving the second type of kininogen using the same protease. For example, a signature peptide of cleaved HMWK (e.g., the heavy chain or the light chain, such as the 46 kDa light Example signature peptides for HMWK (e.g., the full-length HMWK) includes, but not limited to: GHEKQRKH (SEQ ID NO: 6), which may be generated by chymotrypsin digestion; KQRKHNLGHGHKHE (SEQ ID NO: 7) and SYYFDLTDGLS (SEQ ID NO: 10), which may be produced by Glu-C digestion; DWGHKQRKH NLGHGHKHER (SEQ ID NO: 8); which may be produced by Asp-N digestion, and HNLGHGHK (SEQ ID NO: 9), which may be produced by Lys-C digestion.

Levels of the digested peptides of interest can be measured using a suitable approach as known in the art or described herein. In some embodiments, such peptides of interested can be measured by an immunoassay using antibodies specific to the peptides of interest, for example, antibodies specific to KHNLGHGH (SEQ ID NO: 1), SSRIGE (SEQ ID NO: 5) and/or SYYFDLTDGLS (SEQ ID NO: 10). Immune assays that can be used for assessing levels of peptides of interest as described herein include Western blots, enzyme linked immunosorbent assays (ELISAs) (e.g., sandwich ELISAs), radioimmunoassays, electrochemiluminescence-based detection assays, and related techniques. Assays, e.g., Western blot assays, may further involve use of a quantitative imaging system, e.g., LICOR imaging technology, which is commercially available (see, e.g., the Odyssey® CLx infrared imaging system from LI-COR Biosciences). In some embodiments, an electrochemiluminescence detection assay or an assay relying on a combination of electrochemiluminescence and patterned array technology is used (e.g., an ECL or MULTI-ARRAY technology assay from Meso Scale Discovery (MSD)).

As used herein, the terms "measuring" or "measurement," or alternatively "detecting" or "detection," means assessing the presence, absence, quantity or amount (which can be an effective amount) of a substance within a sample, including the derivation of qualitative or quantitative concentration levels of such substances, or otherwise evaluating the values or categorization of a subject's.

An antibody that "specifically binds" to a peptide of interest a term well understood in the art, and methods to determine such specific binding are also well known in the art. An antibody is said to exhibit "specific binding" if it reacts or associates more frequently, more rapidly, with greater duration and/or with greater affinity with a particular target peptide than it does with alternative peptides. It is also understood by reading this definition that, for example, an antibody that specifically binds to a first target peptide may or may not specifically or preferentially bind to a second target peptide. As such, "specific binding" or "preferential binding" does not necessarily require (although it can include) exclusive binding. Generally, but not necessarily, reference to binding means preferential binding. In some examples, an antibody that "specifically binds" to a target peptide or an epitope thereof may not bind to other peptides or other epitopes in the same antigen.

As used herein, the term "antibody" refers to a protein that includes at least one immunoglobulin variable domain or immunoglobulin variable domain sequence. For example, an antibody can include a heavy (H) chain variable region (abbreviated herein as $V_H$), and a light (L) chain variable region (abbreviated herein as $V_L$). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')$_2$, Fd fragments, Fv fragments, scFv, and domain antibodies (dAb) fragments (de Wildt et al., Eur J Immunol. 1996; 26(3):629-39)) as well as complete antibodies. An antibody can have the structural features of IgA, IgG, IgE, IgD, IgM (as well as subtypes thereof). Antibodies may be from any source, but primate (human and non-human primate) and primatized are preferred.

In some embodiments, the antibodies as described herein can be conjugated to a detectable label and the binding of the detection reagent to the peptide of interest can be determined based on the intensity of the signal released from the detectable label. Alternatively, a secondary antibody specific to the detection reagent can be used. One or more antibodies may be coupled to a detectable label. Any suitable label known in the art can be used in the assay methods described herein. In some embodiments, a detectable label comprises a fluorophore. As used herein, the term "fluorophore" (also referred to as "fluorescent label" or "fluorescent dye") refers to moieties that absorb light energy at a defined excitation wavelength and emit light energy at a different wavelength. In some embodiments, a detection moiety is or comprises an enzyme. In some embodiments, an enzyme is one (e.g., β-galactosidase) that produces a colored product from a colorless substrate.

In other embodiments, the peptides of interest as described herein may be measured by a liquid chromatography-mass spectrometry (LC-MS) approach, which is an analytical technique that combines the physical separation capabilities of liquid chromatography with the mass analysis capabilities of mass spectrometry (MS).

Multiple reaction monitoring (MRM)—mass spectrometry is a highly sensitive and selective method for the targeted quantitation of protein/peptide abundances in complex biological samples. MRM mass spec has commonly been used for the analysis of small molecules. Here, MRM enables quantification of proteins in complex mixture providing a sensitive and selective tool to validate candidate biomarkers in a disease process. For this approach, a suitable instrument such as an ABSciex 5500 or 6500 QTrap mass spectrometer can be used and differences between various types of plasma samples were assessed after method optimization. Individual plasma samples were digested with a suitable protease such as chymotrypsin or Glu-C to obtain signature peptides for cleaved HWMK or HWMK as described herein.

The level (e.g., concentration) of each signature peptide (e.g., represented by AUC) can be determined via conventional method. When necessary, a ratio of a signature peptide for cleaved HMWK as relative to full-length HMWK to a signature peptide for HMWK as relative to LMWK can be calculated accordingly. Such a ratio can be used to differentiating the presence of cleaved HMWK versus full-length HMWK.

For example, the concentration of a signature peptide for the 46 kDa light chain of the 2-chain HMWK, KHNLGHGH (SEQ ID NO: 1) generated by chymotrypsin digestion, was found to be much higher in plasma samples from HAE patients as relative to plasma samples from healthy human subjects. These results indicate that the 46 kDa light chain of the 2-chain HMWK, represented by a signature peptide of such, is a reliable biomarker for HAE diagnosis and prognosis.

In another example, due to the confirmation of all peptides including HMWK vs LMWK signature peptide, SYYFDLTDGLS (SEQ ID NO: 10) by MRM on Glu C digested HMWK standard and samples, it was discovered in the present studies that the targeted peptides found in plasma are attributed to HMWK. A significant increase in SSRIGE (SEQ ID NO: 5) peptide in HAE SCAT plasma was observed when compared with normal SCAT plasma and an increase was also observed between plasma activated by FXIIa versus non-activated plasma, with no change in HMWK peptide. Also the ratios between SSRIGE (SEQ ID NO: 5)/SYYFDLTDGLS (SEQ ID NO: 10) was found to be higher in HAE SCAT plasma samples when compared to normal SCAT plasma samples and also in activated versus non-activated plasma. The relative abundance ratios using ratio for SSRIGE (SEQ ID NO: 5) and SYYFDLTDGLS (SEQ ID NO: 10) was 4.4 and 8.9 for normal SCAT plasma versus HAE SCAT plasma respectively and 19.02 and 48.63 for Normal citrated and citrate activated by FXIIa, respectively.

The kininogen deficient plasma (a negative control) sample showed low intensity peak near the detection limits for SSRIGE (SEQ ID NO: 5) peptide which was expected possibly due to presence of LMWK. HMWKlong peptide, KKIYPTVNC QPLGMISLMKRPPGFSPFRSSRIGE (SEQ ID NO: 18) in plasma samples was also measured using targeted assay (MRM). There was almost no change in HMWK long peptide between normal SCAT and HAE SCAT plasma samples and between activated and non-activated samples.

II. Kit

The present disclosure also provides kits for use in measuring the level of a signature peptide for cleaved HMWK and/or for differentiating cleaved HMWK versus full-length HMWK in a sample, e.g., biological samples from human patients. Such kits can comprise one or more of a suitable protease (e.g., chymotrypsin or Glu C), detecting agent specific to signature peptides, which can be generated by digestion of the suitable protease, an evacuated blood collection tube, and optionally, standard cleaved kininogen and/or intact kininogen as controls. In some embodiments, the kits further comprise secondary antibodies and/or reagents for detecting binding of the detection reagent to the peptides of interest.

In some embodiments, the kit can comprise instructions for use in accordance with any of the methods described herein. The included instructions can comprise a description of how to use the components contained in the kit for measuring the level of a signature peptide in a sample treated by a protease.

The instructions relating to the use of the kit generally include information as to the amount of each component and suitable conditions for performing the assay methods described herein. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the kit is used for measuring the level of a signature peptide for cleaved HMWK and/or for differentiating cleaved HMWK versus full-length HMWK. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like.

Kits may optionally provide additional components such as buffers and interpretive information. Normally, the kit comprises a container and a label or package insert(s) on or associated with the container. In some embodiments, the present disclosure provides articles of manufacture comprising contents of the kits described above.

III. Application of Assay Methods (i) Clinical Applications: Disease Diagnosis and Prognosis Approximately 75-90% of circulating prekallikrein is bound to HMWK through a non-active site interaction with domain 6 of HMWK. Free and HMWK-bound active pKal generate cleaved HMWK and bradykinin. The suitability of a biomarker can be demonstrated by following its levels in the presence and absence of an acute attack of HAE. Levels of these biomarkers could also be altered during an attack of bradykinin mediated edema or other disease mediated by pKal activity.

The assay methods and kits described herein can be applied for evaluation of disease, e.g., diagnosis or prognosis of a disease. Evaluation may include identifying a subject as being at risk for or having a disease as described herein, e.g., a pKal-mediated disorder such as HAE. Evaluation may also include monitoring treatment of a disease, such as evaluating the effectiveness of a treatment for a PKal-mediated disorder such as HAE. Further, evaluation may include identifying a disease that can be treated by a pKal inhibitor.

A. Diagnosis

In some embodiments, the assay methods and kits are performed to determine the level of cleaved kininogen and/or intact kininogen in a biological sample (e.g., a blood sample or a plasma sample) collected from a candidate subject (e.g., a human patient suspected of having a PKal-mediated disorder such as HAE. The level of cleaved HMWK (e.g., the 2-chain HMWK, or the heavy and/or light chain thereof, including the 56 kDa light chain and the 46 kDa light chain) and/or a ratio between the level of cleaved HMWK versus the intact HMWK can be determined based on the level of a signature peptide for cleaved HMWK as described herein and/or a ratio between the signature peptide for cleaved HWMK and a signature peptide for HMWK (e.g., as relative to LMWK) described herein. Such a signature peptide concentration or a ratio can be compared to a predetermined reference value or reference ratio to determine whether the subject has or is at risk for the PKal-mediated disorder, e.g., HAE. For example, if the signature peptide concentration or the ratio of two signature peptides in sample of a candidate subject is at or higher than a reference value/ratio, the subject can be identified as having or at risk for a pKal-mediated disorder such as HAE.

The reference value/ratio can be a control level of the signature peptide or a ratio of two signature peptide as described herein. In some embodiments, the control value/ratio represents the value/ratio of signature peptide(s) in a control sample, such as a sample (e.g., blood or plasma sample) obtained from a healthy subject or population of healthy subjects, which preferably are of the same species as the candidate subject. As used herein, a healthy subject is a subject that is apparently free of the target disease (e.g., a PKal-mediated disorder such as HAE at the time the level of cleaved and/or intact kininogen is measured or has no history of the disease.

In some embodiments, the control sample can be obtained from human HAE patients who are in quiescent disease stage. An elevated level of a signature peptide for cleaved HMWK or an elevated ratio between a signature peptide for cleaved HMWK and a signature peptide for HMWK as relative to a reference value/ratio obtained from such control samples may indicate risk of HAE attack.

The reference value/ratio can also be a predetermined value or ratio. Such a predetermined value/ratio can represent the value of a signature peptide for cleaved HWMK (e.g., a signature peptide for the 46 kDa light chain of the 2-chain HMWK) or the ratio of two signature peptides as described herein in a population of subjects that do not have or are not at risk for the target disease. It can also represent the value (e.g., concentration) of the signature peptide for cleaved HWMK (e.g., the 46 kDa light chain) or the ratio of two signature peptides as described herein in a population of subjects that have the target disease (e.g., in quiescent disease stage).

The predetermined value/ratio can take a variety of forms. For example, it can be single cut-off value, such as a median or mean. In some embodiments, such a predetermined level can be established based upon comparative groups, such as where one defined group is known to have a target disease and another defined group is known to not have the target disease. Alternatively, the predetermined level can be a range, for example, a range representing the ratio of two peptides of interest in a control population within a predetermined percentile.

The control value/ratio as described herein can be determined by routine technology. In some examples, the control value/ratio can be obtained by performing a conventional method (e.g., the same assay for obtaining the level of two peptides of interest in a test sample as described herein) on a control sample as also described herein. In other examples, levels of the signature peptides of interest can be obtained from members of a control population and the results can be analyzed by, e.g., a computational program, to obtain the control level (a predetermined level) that represents the level of cleaved and/or intact kininogen in the control population.

By comparing the concentration of a signature peptide for cleaved HWMK as described herein or the ratio of two signature peptides of interest as also described herein in a sample obtained from a candidate subject to the reference ratio as described herein, it can be determined as to whether the candidate subject has or is at risk for the PKal-mediated disease (e.g., HAE), or whether an HAE patient is at risk for an HAE attack. For example, if the value of the signature peptide for cleaved HMWK or the ratio of the two signature peptides of interest in a sample of the candidate subject deviates from the reference value or ratio (e.g., increased as compared to the reference value or ratio), the candidate subject might be identified as having or at risk for the disease, or as an HAE patient at risk for an HAE attack. When the reference value or ratio represents the value or ratio range of the signature peptides of interest as described herein in a population of subjects that have the target disease, the value or ratio of the signature peptides of interest in a sample of a candidate falling in the range indicates that the candidate subject has or is at risk for the target disease.

As used herein, "an elevated value/ratio or a value/ratio above a reference value/ratio" means that the value of a signature peptide or the ratio of two signature peptides is higher than a reference value or ratio, such as a pre-determined threshold ratio of the same signature peptide or the same two signature peptides in a control sample. Control levels are described in detail herein. An elevated value of a signature peptide or an elevated ratio of two signature peptides of interest includes a value/ratio that is, for example, 1%, 5%, 10%, 20%, 30%, 40%, 50%, 60%, 70%, 80%, 90%, 100%, 150%, 200%, 300%, 400%, 500% or more above a reference value/ratio.

As used herein, "a decreased value/ratio below a reference value/ratio" means that the level of a signature peptide or the ratio of two signature peptides of interest is lower than a reference value/ratio, such as a pre-determined threshold of the same signature peptide or the same two signature peptides of interest in a control sample. Control levels are described in detail herein. A decreased value or a signature peptide or the ratio of two signature peptides includes a value/ratio that is, for example, 1%, 5%, 10%, 20%, 30%, 40%, 50%, 60%, 70%, 80%, 90%, 100%, 150%, 200%, 300%, 400%, 500% or more lower than a reference ratio of the two peptides of interest.

In some embodiments, the candidate subject is a human patient having a symptom of a pKal-mediated disorder, e.g., such as HAE. For example, the subject has edema, swelling wherein said swelling is completely or predominantly peripheral; hives; redness, pain, and swelling in the absence of evidence of infection; non-histamine-mediated edema, recurrent attacks of swelling, or a combination thereof. In other embodiments, the subject has no symptom of a pKal-mediated disorder at the time the sample is collected, has no history of a symptom of a pKal-mediated disorder, or no history of a pKal-mediated disorder such as HAE. In yet other embodiments, the subject is resistant to an anti-histamine therapy, a corticosteroid therapy, or both.

B. Evaluate Treatment Effectiveness

The assay methods described herein can also be applied to evaluate the effectiveness of a treatment for a PKal-mediated disorder (e.g., HAE). For examples, multiple biological samples (e.g., blood or plasma samples) can be collected from a subject to whom a treatment is performed either before and after the treatment or during the course of the treatment. The levels of signature peptides can be measured by any of the assay methods as described herein and the level of a signature peptide for cleaved HMWK (e.g., the 46 kDa light chain) or the ratio of a cleaved-HMWK-specific peptide to a HMWK-specific peptide can be determined accordingly. If the value of the signature peptide for cleaved HMWK (e.g., for the 46 kDa) or the ratio of the two signature peptides decreases after the treatment or over the course of the treatment (the level of the signature peptide for cleaved HMWK (e.g., the 46 kDa light chain) or the ratio of the two signature peptides of interest in a later collected sample as compared to that in an earlier collected sample), it indicates that the treatment is effective. In some examples, the treatment involves a therapeutic agent, such as a kallikrein binding agent as described herein, a bradykinin B2 receptor antagonist as described herein, or a C1-INH replacement agent as described herein. Examples of the therapeutic agents include, but not limited to, DX-2930, SHP643 or DX88.

If the subject is identified as not responsive to the treatment, a higher dose and/or frequency of dosage of the therapeutic agent are administered to the subject identified. In some embodiments, the dosage or frequency of dosage of the therapeutic agent is maintained, lowered, or ceased in a subject identified as responsive to the treatment or not in need of further treatment. Alternatively, a different treatment can be applied to the subject who is found as not responsive to the first treatment.

(ii) Non-Clinical Applications

Further, the assay methods described herein have non-clinical applications, for example, for research purposes and/or pre-clinical drug development purposes. Although many diseases associated with pKal have been identified, it is possible that other diseases are mediated by similar mechanisms or involve similar components. In some embodiments, the methods described herein may be used to identify a disease as being associated with pKal. In some embodiments, the methods described herein may be used to study mechanisms (e.g., the discovery of novel biological pathways or processes involved in disease development) or progression of a disease.

In some embodiments, the level or ratio of signature peptides determined by the assay methods as described herein may be relied on in the development of new therapeutics for a disease associated with pKal. For example, the level or ratio of signature peptides as described herein may be measured in samples obtained from a subject having been administered a new therapy (e.g., a clinical trial), or in samples obtained from in vitro assays. In some embodiments, the level or ratio of the signature peptides may indicate the activity of the new therapeutic in in vitro assays or the efficacy of the new therapeutic in clinical trial settings.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Methods for Differentiating Cleaved High Molecular Weight Kininogen (HMWK) from Full-Length HMWK The overall goal of this example was to develop a robust method for LC-MS based peptide quantitation assay to differentiate full-length kininogen (HK; single chain or 1-chain HK) and kallikrein cleaved kininogen (two-chain product or 2-chain HK, as well as the heavy and/or light chains of the two-chain product). In some examples, this semi-quantitative assay measured the ratio of 2-chain HK product to 1-chain HK substrate to determine a 2-chain HK cut-point in a biological sample (e.g., plasma) of healthy volunteers as compared to patients with disease associated with plasma kallikrein such as HAE.

Single chain HMWK (1-chain HK) and two chain HMWK (2HK) (Enzyme Research Laboratories and Sigma) were used as standards in the examples described below. Different types of plasma samples (Citrate, Citrate+Protease inhibitor (PI), normal SCAT plasma (heathy subject plasma samples collected in SCAT tubes), and HAE SCAT plasma (HAE patient plasma samples collected in SCAT tubes) were used in the examples described below. See, e.g., PCT/US2016/046681, the relevant disclosures therein are incorporated by reference herein. Quality controls were run between runs and reproducibility checks were performed for processing variability on different days and on different runs. EDTA-Plasma (Biochem Services) was used as a control for method optimization.

The assay described and developed in this example provides a sensitive and selective method to validate candidate biomarkers in a disease process. For this approach an ABSciex 5500 or 6500 QTrap mass spectrometer was used and differences between various types of plasma samples was assessed after method optimization. Individual plasma samples (including normal SCAT and HAE SCAT plasma, kininogen deficient plasma, normal citrated plasma, normal citrated plasma activated with factor XIIa and HK standards) were digested with Glu C and multiple reaction monitoring (MRM) analysis was done on the peptides of interest. Glu C was used as an exemplary protease to obtain unique peptides differentiating 1-chain HK from 2-chain HK (signature peptides). Briefly, initial experiments were designed to verify quality of the protein standards using MRM mode for specific peptides. 10 µl of sample containing 10 µg of protein was loaded onto the C18 column. Precursor and protease digestion product ions predicted by Skyline software that were unique to the Glu C digested plasma kininogen were selected. The target candidate peptides,

```
                                   (SEQ ID NO: 5)
SSRIGE, (SEQ ID NO: 19)
SSRIGEIKE mis 2, (SEQ ID NO: 20)
KKIYPTVNCQPLGMISLMKRPPGFSPFRSSRIGE, (SEQ ID NO: 21)
KKIYPTVNCQPLGMISLMK,
and (SEQ ID NO: 10)
SYYFDLTDGLS,
``` and 3-5 product ions were validated empirically for plasma kininogen. The fragmentation energy and collision energy were individually optimized to the peptides after using skyline for guidance to perform the MRM. Data was analyzed using Analyst Software (ABSciex). The method development focused on optimizing sample preparation, enzyme digestion on different types of plasma samples and HK standards, chromatography, and mass spectrometry parameters.

(i) Immunoprecipitation Samples Versus Whole Plasma Samples

To validate proof of concept studies, 4 protein samples obtained by immunoprecipitation (IP samples) and 4 whole plasma samples (non-IP samples) were used for the studies. The samples were eluted with SDS, which was then removed by detergent removal column. Targeted assays were performed on an AB Sciex 5500 Qtrap triple quad mass spectrometer to examine peptides of interest in the samples.

All four peptides of interest, SSRIGE (SEQ ID NO: 5), SSRIGEIKE (SEQ ID NO: 19), KKIYPTVNC QPLGMIS-LMKRPPGFSPFRSSRIGE (SEQ ID NO: 18), and KKIYPTVNCQPLGMISLMK (SEQ ID NO: 21), were found in the non-IP samples but were not detected in the IP plasma samples. There were no peak differences found between the activated plasma samples (treated by FXIIa) and non-activated plasma samples. Table 2 below shows the peak intensities of the peptides in the IP and non-IP samples. There was no difference in the peak intensity for SSRRIGE (a peptide unique to the light chain of 2HK generated by Glu C digestion; SEQ ID NO: 22) or KKIYPTVNC QPLGMIS-LMKRPPGFSPFRSSRIGE (a peptide unique to the HK long peptide generated by Glu C digestion; SEQ ID NO: 18) in the activated or non-activated samples (boxed rows).

EDTA plasma was run as a positive control with the IP/non-IP samples, and all peptides of interest were found in both types of samples.

TABLE 2

Peak intensities of 5 peptides of interest in IP and non-IP samples

| Sample type | SSRIGE intensity (RT) | SSRIGEIKE mis 2 intensity (RT) | RPPG ESPER intensity (RT) | KKIYP TVNCQPL GMISLMK intensity (RT) | Long HK peptide intensity (RT) |
|---|---|---|---|---|---|
| Old Plasma | 6000 (5.1) | 1.2E4 (5.8) | x | 600 (17.5) | 6.4E4 (16.5) |
| Sample 1 (HMW) | 4800 (4.5) | 3000 (5) | x | 1300 (17.7) | 2900 (15.5) |
| Sample 2 (LMW) | 2.9E4 (4.6) | 6500 (5) | x | 2380 (17.7) | 7400 (15.4) |
| Sample 3 (normal human Plasma) | 4.7E4 (4.8) | x | x | x | 9000 (15.3) |
| Sample 4 (Activated human Plasma) | 4.2E4 (4.8) | x | x | x | 9000 (15.2) |
| Sample 5 (HMW-IP) | x | x | x | x | x |
| Sample 6 (LMW-IP) | x | x | x | x | x |
| Sample 7 (normal human Plasma-IP) | 500 (4.5) high one transition | 1.4E4 (5.1) | x | x | x |
| Sample 8 (Activated human Plasma-IP) | 640 (4.5) | 2.2E4 (5) high one transition | x | x | x |

The results demonstrated that a whole plasma sample digest with Glu C provided enough sensitivity to detect both 1-chain HK and 2-chain HK peptides. Therefore, whole plasma samples digested by the exemplary Glu C protease was used in the experiments described below.

(ii) Sample Preparation Optimization
   (a) Digestion Protocols
   To optimize the plasma Glu C digestion, various protocols were used to optimize the GluC digestion. Different parameters of the protocol were modified as summarized below:
      Protocol 1: adding denaturation step before digestion (in the presence of DTT at, e.g., 0.1 M)
      Protocol 2: using different concentration of reducing agent (0.05 M DTT).
      Protocol 3: 10-time dilution of sample before digestion; and
      Protocol 4: increased enzyme incubation time to 19 hours.
   Protocol 2 resulted in better detection of SSRIGE (SEQ ID NO: 5) and KKIYPTVNCQPLGMISLMK (SEQ ID NO: 21), based on peak intensities and peak shapes. Accordingly, Protocol 2 digestion method was used in subsequent experiments.
   (b) Reduction Temperature and Incubation Time
   The reduction temperature and incubation times were also optimized. Briefly, HK standards and EDTA-plasma were used to evaluate temperatures (55° C. vs 90° C.) and incubation times (30 mins vs 60 mins) for reducing sample during digestion.
      HK: 90° C. for 1 hour
      HK: 55° C. for 30 minutes
      Plasma EDTA (Biochem): 90° C. for 1 hour
      Plasma EDTA (Biochem): 55° C. for 30 minutes
   The samples were analyzed by sing multiple reaction monitoring (MRM) analysis, detecting SSRIGE (SEQ ID NO: 5) and KKIYPTVNCQPLGMISLMKRPPGFSP-FRSSRIGE (SEQ ID NO: 20) peptides. The peak intensities were found to be higher in samples (both HK standard samples and plasma samples) reduced at 90° C. for 1 hr as compared to the samples reduced at 55° C. for 30 mins. Conditions including incubation at 90° C. for 1 hr were used for reducing samples in subsequent experiments.
   (c) Protease Inhibitors (PI) and Anticoagulants in Plasma
   The effects of the presence of PI and anticoagulants in the plasma on the digestion efficiency were also evaluated. Digestion efficiency was assessed for plasma with and without PI and also between plasma containing citrate as anticoagulant versus EDTA. The samples were evaluated by MRM analysis using the AB Sciex 5500 Qtrap LC-MS/MS System, and the peak intensities were compared for SSRIGE (SEQ ID NO: 5), indicated with arrow in FIG. 3. These results demonstrated that:
      Plasma EDTA without PI>Plasma EDTA with PI>Plasma Citrated without PI>Plasma Citrated with PI.
   These results also indicated that citrate and protease inhibitors have negative effect on the Glu C digestion, as a decreased response of peptide was seen in the samples containing citrate, PI or both.
(iii) Different Enzyme Digestion to Check Sequence Coverage
   To examine whether the sequence coverage was enzyme dependent, a different enzyme, trypsin, was used. HK standard sample from Sigma and EDTA-plasma sample from Biochem were digested with trypsin and ran on high resolution accurate mass instrument (HRAM) and analysis was done using proteome discoverer. The results were analyzed using Proteome Discoverer™ software.
   Full length kininogen was detected in both HK and plasma samples digested with trypsin with good sequence coverage.

(iv) Single Ion Monitoring (SIM) of EDTA-Plasma and HK Samples
   HK and plasma samples having higher concentrations were used for SIM, and peptides of interest were detected using a high resolution accurate mass (HRAM) instrument. SIM-MS$^2$ data analysis was performed on EDTA plasma and HK sigma samples.
   Analysis of the Glu C digested EDTA plasma samples on HRAM instrument resulted in detection of all four peptides, SSRIGE (SEQ ID NO: 5), KKIYPTVNCQPLGMISLMK (SEQ ID NO: 21), HK long peptide and Bradykinin. Regarding the HK standard sample, the peptides SSRIGE (SEQ ID NO: 5), KKIYPTVNCQPLGMISLMK (SEQ ID NO: 21) and Bradykinin were found but not the HK long peptide.
   To confirm the identity of the standards, two different sources of HK were used (Enzyme research and Sigma). However, there was no detectable difference observed between the two standards in this experiment, and the HK long peptide was not detected in either standard sample.
(v) Different Types of Plasma, Different Glu C and Different Enzyme to Protein Ratio
   In order to further optimize the Glu C digestion, different types of plasma samples (EDTA, citrated, with and without PI), different Glu C sources (Protea & Promega), and different enzyme:protein ratios (1:20 & 1:10) were assessed. Additionally, various detection platforms including full scan, SIM-MS$^2$ (on HRAM), MRM (on QQQ; triple Quad instrument) were used to detect the peptides of interest in the different samples. Table 3 shows the summary of the various combinations of sample type, enzyme and dilution used for this experiment.

TABLE 3

Summary of conditions tested

| Sample Type | Enzymes used for Digestion | Enzyme:Protein |
|---|---|---|
| EDTA Plasma (Biochem) | Protea Glu C and Promega Glu C | 1:20 and 1:10 |
| Citrated Plasma (Sponsor) | Protea Glu C and Promega Glu C | 1:20 and 1:10 |
| HK Sigma | Protea Glu C and Promega Glu C | 1:20 and 1:10 |
| EDTA Plasma (Biochem) + PI | Protea Glu C and Promega Glu C | 1:20 |
| Citrated Plasma (Sponsor) + PI | Protea Glu C and Promega Glu C | 1:20 |

(a) Full Scans and SIM-MS$^2$ (HRAM)
   Different types of plasma and standard samples noted above were digested with Glu C and the digestion produces were run on HRAM instrument for full scans and SIM-W. Sample information is shown on the right hand side of the legend color map. Analysis was performed using Proteome Discoverer™ software and Xcalibur™ software to determine the peak intensities for each of the peptides of interest.
   For plasma samples, the following response of peptide intensities for SSRIGE (SEQ ID NO: 5) was observed:
      Plasma EDTA without PI>Plasma EDTA with PI>Plasma citrated without PI>Plasma citrated with PI.

It was determined that the 1:20 (enzyme:protein) ratio resulted in a better response than 1:10 (enzyme:protein) ratio. For the HK long peptide, the intensities were only minimally affected by the type of plasma or enzyme:protein ratio. The HK long peptide was not observed in any of the standard samples; however the KKIYPTVNCQPLGMIS-LMK peptide (SEQ ID NO: 23) and bradykinin were detected in all standards, indicating that the HK long peptide may be degrading. Without being bound by any particularly theory, this may explain the observation of various fragments of HK long peptides, including

KKIYPTVNCQPLGMISLMK, (SEQ ID NO: 21)

RPPGFSPFR, (SEQ ID NO: 24)
and

SSRIGE. (SEQ ID NO: 5)

Table 4 below shows the intensities of peptides of interest using full scans and SIM-MS$^2$ data on HRAM instrument (sorted by sample kind).

TABLE 4

Intensities of Peptides of Interests

| Sample type | SSRIGE (SEQ ID NO: 5) | SSRIGEIKEmis$^2$ (SEQ ID NO: 19) | KKIYPTVNCQP LGMISLMK (SEQ ID NO: 21) | bradykinin | KKIYPTVNCQP LGMISLMKRPP GFSPFRSSRIGE (SEQ ID NO: 20) |
|---|---|---|---|---|---|
| A1: Plasma EDTA (Biochem) Protea Glu C 1:20 | ++++ | +/- | +++ | - | ++++ |
| B1: Plasma EDTA (Biochem) Promega Glu C 1:20 | ++++ | +/- | +++ | - | ++++ |
| E1: Plasma EDTA (Biochem) Protea Glu C 1:10 | +++ | +/- | +++ | - | ++++ |
| F1: Plasma EDTA (Biochem) Promega Glu C 1:10 | +++ | +/- | +++ | - | ++++ |
| A2: Plasma Citrated, Protea Glu C:1:20 | ++++ | +/- | +++ | - | ++++ |
| B2: Plasma Citrated, Promega Glu C:1:20 | ++++ | +/- | +++ | - | ++++ |
| E2: Plasma Citrated, Protea Glu C:1:10 | +++ | +/- | +++ | - | ++++ |
| F2: Plasma Citrated, Promega Glu C:1:10 | +++ | +/- | +++ | - | ++++ |
| C1: Plasma EDTA (Biochem) + PI, protea Glu C 1:20 | ++ | +/- | +++ | - | ++++ |
| C2: Plasma citrated + PI, proea Glu C | ++ | +/- | +++ | - | ++++ |

TABLE 4-continued

Intensities of Peptides of Interests

| Sample type | SSRIGE (SEQ ID NO: 5) | SSRIGEIKE-mis$^2$ (SEQ ID NO: 19) | KKIYPTVNCQP LGMISLMK (SEQ ID NO: 21) | bradykinin | KKIYPTVNCQP LGMISLMKRPP GFSPFRSSRIGE (SEQ ID NO: 20) |
|---|---|---|---|---|---|
| 1:20 | | | | | |
| D1: Plasma EDTA (Biochem) PI, Promega Glu C 1:20 | ++ | +/- | +++ | - | ++++ |
| D2: Plasma citrated + PI, promega Glu C 1:10 | ++ | +/- | +++ | - | ++++ |
| A3: HK Sigma, Protea Glu C 1:20 | ++++ | +/- | +++ | + | - |
| B3: HK Sigma, Promega Glu C 1:20 | ++++ | +/- | +++ | + | - |
| E3: HK Sigma, Protea Glu C 1:10 | +++ | +/- | +++ | + | - |
| F3: HK Sigma, Promega Glu C 1:10 | +++ | +/- | +++ | + | - |

++++: High abundance
+++: Medium abundance
++: low abundance
+: very low abundance
+/-: Negligible abundance
-: Absent (b) Multiple Reaction Monitoring (MRM) Targeted Assay The same set of samples described above was used to detect the peptides of interest using a targeted assay (MRM). The samples were analyzed using AB Sciex Analyst software following detection using an AB Sciex Qtrap 5500 instrument. Sample information is presented on the right hand side of color map.

Detection of the SSRIGE peptide (SEQ ID NO: 5) was consistently observed regardless of sample type and condition. With the optimized sample preparation, the SSRIGEKE (SEQ ID NO: 25) peptide was not detected. However, the HK long peptide was present only in plasma samples but not in HK standard samples. The KKYIPTVNCQPLGMISLMK (SEQ ID NO: 23) peptide and bradykinin peptide were present in all HK standard samples, but no HK long peptide was detected. These results were similar to the data set from full scan and MS$^2$ described above, and suggest that the HK long peptide may be degraded, further explaining the observation of the HK long peptide fragments noted above.

Table 5 below shows the intensities of peptides of interest using MRM data on AB Sciex Qtrap 5500 instrument (sorted by sample list).

TABLE 5

Intensities of Peptides of Interests

| Sample type | SSRIGE (SEQ ID NO: 5) | SSRIGEIKE-mis$^2$ (SEQ ID NO: 19) | KKIYPTVNCQP LGMISLMK (SEQ ID NO: 21) | bradykinin | KKIYPTVNCQP LGMISLMKRPP GFSPFRSSRIGE (SEQ ID NO: 20) |
|---|---|---|---|---|---|
| A1: Plasma EDTA (Biochem) Protea Glu C 1:20 | ++++ | - | +++ | +/- | ++++ |
| A2: Plasma Citrated, Protea Glu C:1:20 | ++++ | - | +++ | - | ++++ |

TABLE 5-continued

Intensities of Peptides of Interests

| Sample type | SSRIGE (SEQ ID NO: 5) | SSRIGEIKE-mis² (SEQ ID NO: 19) | KKIYPTVNCQP LGMISLMK (SEQ ID NO: 21) | bradykinin | KKIYPTVNCQP LGMISLMKRPP GFSPFRSSRIGE (SEQ ID NO: 20) |
|---|---|---|---|---|---|
| A3: HK Sigma, Protea Glu C 1:20 | ++++ | - | +++ | + | - |
| B1: Plasma EDTA (Biochem) Promega Glu C 1:20 | ++++ | - | +++ | - | ++++ |
| B2: Plasma Citrated, Promega Glu C:1:20 | ++++ | - | +++ | - | ++++ |
| B3: HK Sigma, Promega Glu C 1:20 | ++++ | - | +++ | + | - |
| C1: Plasma EDTA (Biochem) + PI, protea Glu C 1:20 | ++++ | - | +++ | - | ++++ |
| C2: Plasma citrated + PI, proea Glu C 1:20 | ++++ | - | +++ | + | ++++ |
| D1: Plasma EDTA (Biochem) PI, Promega Glu C 1:20 | ++++ | - | +++ | - | ++++ |
| D2: Plasma citrated + PI, promega Glu C 1:10 | ++++ | - | +++ | - | ++++ |
| E1: Plasma EDTA (Biochem) Protea Glu C 1:10 | ++++ | - | +++ | - | ++++ |
| E2: Plasma Citrated, Protea Glu C:1:10 | ++++ | - | +++ | - | ++++ |
| E3: HK Sigma, Protea Glu C 1:10 | ++++ | - | +++ | + | - |
| F1: Plasma EDTA (Biochem) Promega Glu C 1:10 | ++++ | - | +++ | - | ++++ |
| F2: Plasma Citrated, Promega Glu C:1:10 | ++++ | - | +++ | - | ++++ |

TABLE 5-continued

Intensities of Peptides of Interests

| Sample type | SSRIGE (SEQ ID NO: 5) | SSRIGEIKE-mis² (SEQ ID NO: 19) | KKIYPTVNCQP LGMISLMK (SEQ ID NO: 21) | bradykinin | KKIYPTVNCQP LGMISLMKRPP GFSPFRSSRIGE (SEQ ID NO: 20) |
|---|---|---|---|---|---|
| F3: HK Sigma, Promega Glu C 1:10 | ++++ | - | +++ | + | - |

++++: High abundance
+++: Medium abundance
++: low abundance
+: very low abundance
+/-: Negligible abundance
-: Absent (c) Sequence Coverage Using HRAM and Proteome Discoverer™ Software In order to determine the optimal Glu C concentration for protein digestion, sequence coverage of HK standard samples was assessed by full scan on a HRAM instrument following digestion with Glu C from different sources (Protea and Promega) and different enzyme: protein concentrations (1:20 and 1:10). The 1:20 dilution of Glu C from either source performed optimally for digestion, as the sequence coverage was more in the area of interest. As provided below, the 1:10 dilution also provided coverage in the area of interest, but the peptide had low confidence score.

(SEQ ID NO: 11)
MKLITILFLCSRLLLSLTQESQSEEIDCNDKDLFKAVDAALKKYNSQNQ

SNNQFVLYRITEATKTVGSDTFYSFKYEIKEGDCPVQSGKTWQDCEYKD

AAKAATGECTATVGKRSSTKFSVATQTCQITPAEGPVVTAQYDCLGCVH

PISTQSPDLEPILRHGIQYFNNNTQHSSLFMLNEVKRAQRQVVAGLNFR

ITYSIVQTNCSKENFLFLTPDCKSLWNGDTGECTDNAYIDIQLRIASFS

QNCDIYPGKDFVQPPTKICVGCPRDIPTNSPELEETLTHTITKLNAENN

-continued
ATFYFKIDNVKKARVQVVAGKKYFIDFVARETTCSKESNEELTESCETK

KLGQSLDCNAEVYVVPWEKKIYPTVNCQPLGMISLMK*RPPGFSPFR*SS

RIGEIKEETTVSPPHTSMAPAQDEERDSGKEQGHTRRHDWGHEKQRKHN

LGHGHKHERDQGHGHQRGHGLGHGHEQQHGLGHGHKFKLDDDLEHQGGH

VLDHGHKHKHGHGHGKHKNKGKKNGKHNGWKTEHLASSSEDSTTPSAQT

QEKTEGPTPIPSLAKPGVTVTFSDFQDSDLIATMMPPISPAPIQSDDDW

IPDIQIDPNGLSFNPISDFPDTTSPKCPGRPWKSVSEINPTTQMKESYY

FDLTDGLS

In the above amino acid sequence of 1-chain HMWK, Glu-C derived peptides in boldface were identified with a single ion, whereas the underlined peptides were identified with multiple ions. Bradykinin is italicized and in boldface.

(vi) Sequence Alignment of High Molecular Weight Kininogen (HMWK) and Low Molecular Weight Kininogen (LMWK)

To identify unique peptides for HMWK as compared to LMWK, sequence alignment of these two types of kininogens was performed using UniProt software is provided below (hHMWK: SEQ ID NO: 11; hLMWK: SEQ ID NO: 12):

```
hHMWK    1   MKLITILFLCSRLLLSLTQESQSEEIDCNDKDLFKAVDAALKKYNSQNQSNNQFVLYRIT   60
             ************************************************************
hLMWK    1   MKLITILFLCSRLLLSLTQESQSEEIDCNDKDLFKAVDAALKKYNSQNQSNNQFVLYRIT   60 hHMWK   61   EATKTVGSDTFYSFKYEIKEGDCPVQSGKTWQDCEYKDAAKAATGECTATVGKRSSTKFS  120
             ************************************************************
hLMWK   61   EATKTVGSDTFYSFKYEIKEGDCPVQSGKTWQDCEYKDAAKAATGECTATVGKRSSTKFS  120 hHMWK  121   VATQTCQITPAEGPVVTAQYDCLGCVHPISTQSPDLEPILRHGIQYFNNNTQHSSLFMLN  180
             ************************************************************
hLMWK  121   VATQTCQITPAEGPVVTAQYDCLGCVHPISTQSPDLEPILRHGIQYFNNNTQHSSLFMLN  180 hHMWK  181   EVKRAQRQVVAGLNFRITYSIVQTNCSKENFLFLTPDCKSLWNGDTGECTDNAYIDIQLR  240
             ************************************************************
hLMWK  181   EVKRAQRQVVAGLNFRITYSIVQTNCSKENFLFLTPDCKSLWNGDTGECTDNAYIDIQLR  240 hHMWK  241   IASFSQNCDIYPGKDFVQPPTKICVGCPRDIPTNSPELEETLTHTITKLNAENNATFYFK  300
             ************************************************************
hLMWK  241   IASFSQNCDIYPGKDFVQPPTKICVGCPRDIPTNSPELEETLTHTITKLNAENNATFYFK  300 hHMWK  301   IDNVKKARVQVVAGKKYFIDFVARETTCSKESNEELTESCETKKLGQSLDCNAEVYVVPW  360
             ************************************************************
hLMWK  301   IDNVKKARVQVVAGKKYFIDFVARETTCSKESNEELTESCETKKLGQSLDCNAEVYVVPW  360
```

-continued

```
hHMWK  361  EKKIYPTVNCQPLGMISLMKRPPGFSPFRSSRIGEIKEETTVSPP---------HTSMAP  411
            ********************************************         *
hLMWK  361  EKKIYPTVNCQPLGMISLMKRPPGFSPFRSSRIGEIKEETTSHLRSCEYKGRPPKAGAEP  420 hHMWK  412  AQDEERDSGKEQGHTRRHDWGHEKQRKHNLGHGHKHERDQGHGHQRGHGLGHGHEQQHGL  471
            *   *
hLMWK  421  ASEREVS----------------------------------------------------- hHMWK  412  GHGHKFKLDDDLEHQGGHVLDHGHKHKHGHGHGKHKNKGKKNGKHNGWKTEHLASSSEDS  531
hLMWK  427  ----------------------------------------------------------- hHMWK  532  TTPSAQTQEKTEGPTPIPSLAKPGVTVTFSDFQDSDLIATMMPPISPAPIQSDDDWIPDI  591
hLMWK  427  ----------------------------------------------------------- hHMWK  592  QIDPNGLSFNPISDFPDTTSPKCPGRPWKSVSEINPTTQMKESYYFDLTDGLS         644
hLMWK  427  -----------------------------------------------------------
```

Four peptides were found to be unique to HMWK as compared to LMWK:

1.
SYYFDLTDGLS (SEQ ID NO: 10)

2.
INPTTQMKE (SEQ ID NO: 26)

3.
KQRKHNLGHGHKHE (SEQ ID NO: 7)

4.
EDSTTPSAQTQE (SEQ ID NO: 27)

a. Detecting Unique Peptides for HMWK in HK Samples Using Full Scan and $MS^2$ on HRAM Beginning with the unique peptide SYYFDLTDGLS (SEQ ID NO: 10), full scans and $MS^2$ were run using Glu C-digested HK standard. The full scans and $MS^2$ run on a HRAM instrument and analyzed using Proteome Discoverer™ software. As shown below, the unique peptides for HMWK were detected in the HK standard, suggesting that the HK standard contained HMWK.

(SEQ ID NO: 11)
MKLITILFLCSRLLLSLTQESQSEEIDCNDKDLFKAVDAALKKYNSQNQS

NNQFVLYRITEATKTVGSDTFYSFKYEIKEGDCPVQSGKTWQDCEYKDAA

KAATGECTATVGKRSSTKFSVATQTCQITPAEGPVVTAQYDCLGCVHPIS

TQSPDLEPILRHGIQYFNNNTQHSSLFMLNEVKRAQRQVVAGLNFRITYS

IVQTNCSKENFLFLTPDCKSLWNGDTGECTDNAYIDIQLRIASFSQNCDI

YPGKDFVQPPTKICVGCPRDIPTNSPELEETLTHTITKLNAENNATFYFK

IDNVKKARVQVVAGKKYFIDFVARETTCSKESNEELTESCETKKLGQSLD

CNAEVYVVPWEKKIYPTVNCQPLGMISLMKRPPGFSPFRSSRIGEIKEET

TVSPPHTSMAPAQDEERDSGKEQGHTRRHDWGHEKQRKHNLGHGHKHERD

QGHGHQRGHGLGHGHEQQHGLGHGHKFKLDDDLEHQGGHVLDHGHKHKHG

HGHGKHKNKGKKNGKHNGWKTEHLASSSEDSTTPSAQTQEKTEGPTPIPS

LAKPGVTVTFSDFQDSDLIATMMPPISPAPIQSDDDWIPDIQIDPNGLSF

NPISDFPDTTSPKCPGRPWKSVSEINPTTQMKESYYFDLTDGLS

The position of the HMWK specific peptide is in boldface and underlined in the amino acid sequence of HMWK shown above.

b. Detecting Unique Peptide for HMWK in HK Samples and EDTA Plasma by MRM

To determine the presence of HMWK in the standard and for comparing that with plasma samples, Glu C-digested HK and Glu C-digested plasma were run on an AB Sciex 5500 Qtrap for targeted analysis. The HMWK unique peptide (SYYFDLTDGLS; SEQ ID NO: 10) was detected in both samples using the MRM assay, although the peak intensity of the peptide was lower in plasma compared to HK standards. This was expected due to the complexity and high background noise in plasma. These results confirmed that the peptides were from HMWK.

(vii) Digestion Conditions a. HK and Plasma Digestion with Glu C at 25° C. and 37° C.

The efficacy of digesting HK and plasma samples with Glu C at 25° C. rather than at 37° C. was evaluated. The unique peptide for HMWK was detected in the HK standards, but the HK long peptide was not detected in standards. In order to test whether there was incomplete digestion or that the high temperatures were degrading the HK standard into bradykinin and KKYIPTVNCQPLGMISLMK (specific to the 2HK heavy peptide; SEQ ID NO: 23), plasma and HK samples were digested with Glu C at 25° C. rather than at 37° C. Using MRM analysis, the peptides of interest were targeted and detected, including the HMWK unique peptide. The peak intensities are as follows:

HK_Sigma Glu C 25° C.:

SSRIGE (SEQ ID NO: 5): 5960

KKIYPTVNCQPLGMISLMKRPPGFSPFRSSRIGE (SEQ ID NO: 20): 4000

SYYFDLTDGLS (SEQ ID NO: 10): 7.6 e4

HK_Enzyme Research Glu C 25° C.:

SSRIGE (SEQ ID NO: 5): 4.5 e5

SSRIGEIKE $mis^2$ (SEQ ID NO: 19): 1.5 e5

KKIYPTVNCQPLGMISLMKRPPGFSPFRSSRIGE (SEQ ID NO: 20): 2.3 e5

SYYFDLTDGLS (SEQ ID NO: 10): 4.6 e5

It was found that Glu C digestion of HK standards (from Enzyme Research and Sigma) at 25° C. resulted in detection of all three peptides of interest including the HK long peptide, indicating that the high temperature was degrading the standards and thus the HK long peptide as not observed when digested at 37° C. The standard obtained from the Enzyme Research yielded higher peak intensities as compared to the standard obtained from Sigma. The mis 2 cleaved peptide SSRIGEIKE (SEQ ID NO: 19) was found only in Enzyme Research standard. As to plasma samples, the results indicated that Glu C digestion at 37° C. led to better digestion efficiency than Glu C digestion at 25° C. FIG. 1. Confirmation of the long peptide and other HMWK unique peptides using standard at 25° C. indicate that the peptides observed in plasma samples are from HK.

No peptides except SSRIGE (SEQ ID NO: 5) were detected in plasma samples at 25° C.; however all peptides of interest as expected were observed in plasma samples digested at 37° C. (FIG. 1). The HK long peptide was observed in both standards at 25° C. but not at 37° C.

These results suggested that digestion with Glu C at 25° C. was better for the standard samples, whereas digestion at 37° C. digestion worked better for plasma.

a. Optimized Digestion Method Using High Resolution Accurate Mass Instrument (HRAM)

The 25° C. and 37° C. Glu C-digested samples (both HK and plasma) were also assessed on HRAM instruments for full scans to detect the peptides of interest, including the HK long peptide and the HMWK unique peptides, in order to determine whether another detection platform could be used to detect peptides of interest in plasma samples digested at 25° C.

All peptides of interest and the HMWK unique peptides were detected in HK standard samples digested at 25° C. and in plasma samples digested at 37° C. This data set was consistent with the MRM data described above, except for the mis 2 cleaved peptide SSRIGEIKE (SEQ ID NO: 19), which is usually seen in HK standard from Enzyme Research. The LMWK unique peptide YKGRPPKAGAE (SEQ ID NO: 28) was also included in this assay and was found in plasma samples not the HK standard, consistent with what was expected (FIG. 2. 3).

b. Sequence Coverage of HK-Full Scan at 25° C.

The sequence coverage of HK standard was evaluated using the optimized HK Glu C digestion, Glu C source, and enzyme to protein ratio. Briefly, the Glu C digestion performed at 25° C. with a 1:20 enzyme: protein ratio resulted in a sequence coverage of HK (both sourced from Enzyme Research and Sigma) that was significantly improved with high confidence score, particularly in the region of interest (HK long peptide).

(SEQ ID NO: 11)
MKLITILFLCSRLLLSLTQESQSEEIDCNDKDLFKAVDAALKKYNSQNQS

NNQFVLYRITEATKTVGSDTFYSFKYEIKEGDCPVQSGKTWQDCEYKDAA

KAATGECTATVGKRSSTKFSVATQTCQITPAEGPVVTAQYDCLGCVHPIS

TQSPDLEPILRHGIQYFNNNTQHSSLFMLNEVKRAQRQVVAGLNFRITYS

IVQTNCSKENFLFLTPDCKSLWNGDTGECTDNAYIDIQLRIASFSQNCDI

YPGKDFVQPPTKICVGCPRDIPTNSPELEETLTHTITKLNAENNATFYFK

IDNVKKARVQVVAGKKYFIDFVARETTCSKESNEELTESCETKKLGQSLD

CNAEVYVVPWEKKIYPTVNCQPLGMISLMKRPPGFSPFRSSRIGEIKEET

TVSPPHTSMAPAQDEERDSGKEQGHTRRHDWGHEKQRKHNLGHGHKHERD

-continued

QGHGHQRGHGLGHGHEQQHGLGHGHKFKLDDDLEHQGGHVLDHGHKHKHG

HGHGKHKNKGKKNGKHNGWKTEHLASSSEDSTTPSAQTQEKTEGPTPIPS

LAKPGVTVTFSDFQDSDLIATMMPPISPAPIQSDDDWIPDIQIDPNGLSF

NPISDFPDTTSPKCPGRPWKSVSEINPTTQMKESYYFDLTDGLS

The position of the HK long peptide is in boldface and underlined in the amino acid sequence of HMWK shown above.

c. Full Scan and SIM on HRAM Instrument

SIM and a full scan using a HRAM instrument were also performed on a HK standard digested at 25° C. for detecting the HK long peptide. The HK long peptide was observed in HK standard by full scan and SIM on HRAM instrument following digestion at 25° C.

(viii) HMWK Vs LMWK-Unique Peptides for Glu C at 25° C. Digestion

Two additional unique peptides of HMWK (relative to LMWK), INPTQMKE (SEQ ID NO: 29) and SYYDDGLS (SEQ ID NO: 30), were added, and MRM analysis was performed to detect those unique peptides. Following digestion of the HK standards (HK Sigma and HK_Enzyme Research) at 25° C., the additional HMWK unique peptides were observed, confirming the presence of HK.

(ix) Assessing Differences Between Different Types of Samples with the Optimized Method a. Quantitation of SSRIGE (SEQ ID NO: 5) in Plasma Samples Using Targeted Assay (MRM)

Individual plasma samples were digested with Glu C, and MRM analysis was performed to detect the peptide of interest, SSRIGE (SEQ ID NO: 5). The sample types included normal SCAT and HAE SCAT plasma samples, kininogen-deficient plasma samples, normal citrated plasma samples, normal citrated plasma samples activated with Factor XIIa, and HK standard samples.

Figure 3:
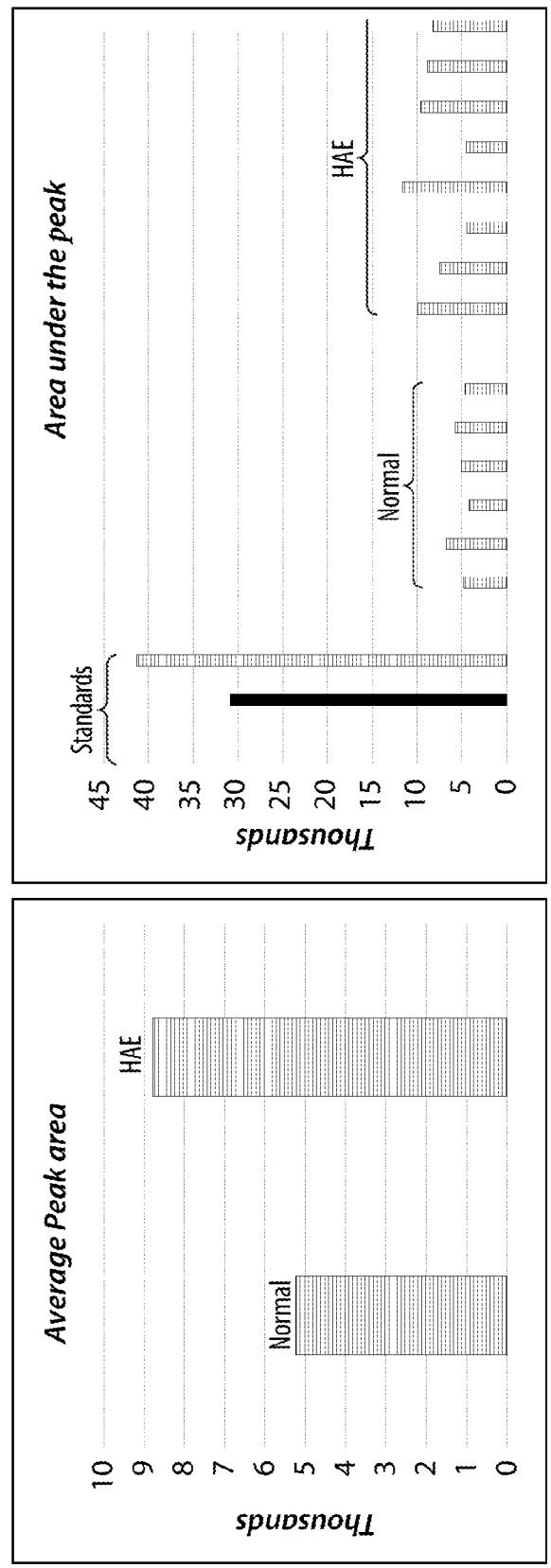
FIG. 3 includes charts showing quantitation of peptide SSRIGE (SEQ ID NO: 5) derived from protease digestion of the 56 kDa light chain in normal and HAE plasma samples using targeted assay MRM.

As shown in Figure. 3, the SSRIGE (SEQ ID NO: 5) peptide was quantified using quantitation wizard of analyst software. A significant increase of the SSRIGE (SEQ ID NO: 5) peptide was detected in the HAE SCAT plasma samples as compared to the normal SCAT plasma samples. There was also a noticeable increase of SSRIGE (SEQ ID NO: 5) peptide in the activated plasma as compared to non-activated plasma samples. The kininogen-deficient plasma sample showed minimal SSRIGE (SEQ ID NO: 5) peptide, which was expected since HMWK is absent.

b. Quantitation of HK Long Peptide in Plasma Samples Using Targeted Assay (MRM)

Figure 4:
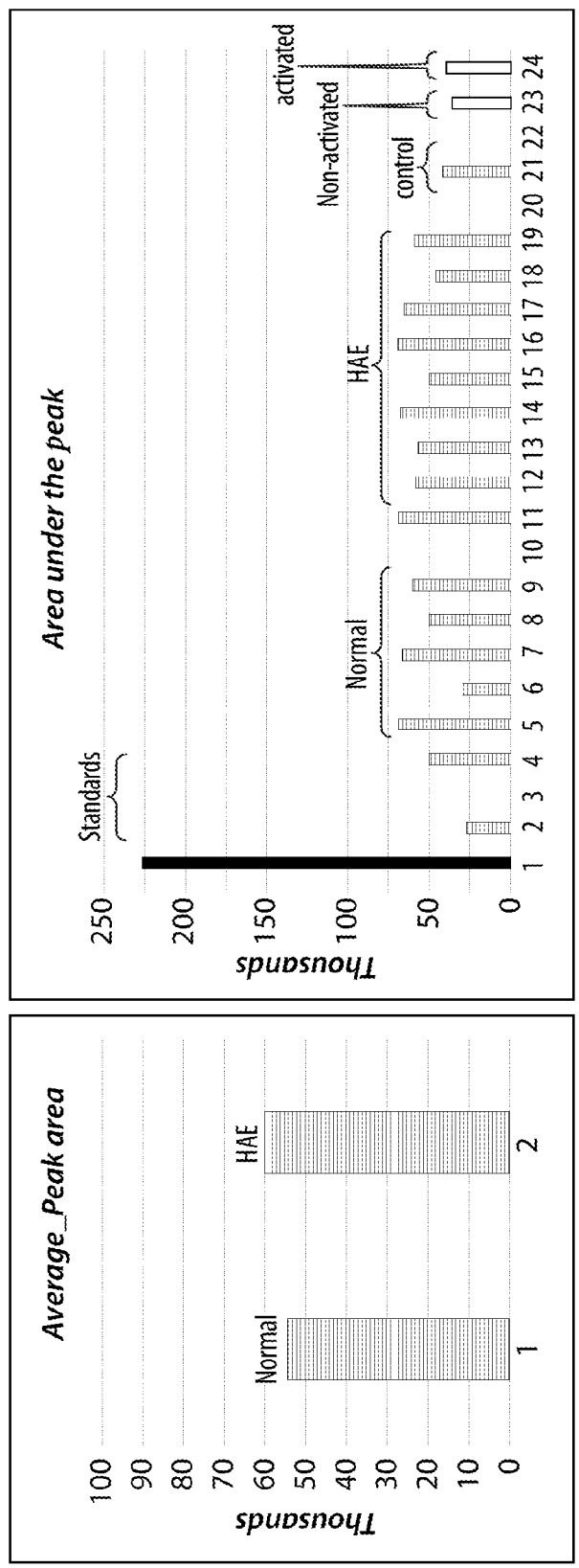
FIG. 4 includes charts showing quantitation of HMWK long peptide in normal and HAE plasma samples using targeted assay MRM.

Plasma samples were digested with Glu C, and MRM analysis was performed to detect the HK long peptide. The sample types included normal SCAT and HAE SCAT plasma samples, kininogen-deficient plasma samples, normal citrated plasma samples, normal citrated plasma samples activated with Factor XIIa, and HK standards. There was very minimal change in HK long peptide detected between normal SCAT and HAE SCAT plasma samples. Additionally, no difference was observed between activated and non-activated samples. FIG. 4.

(x) Evaluation of the Consistency and Reproducibility for Glu C Digestion

To evaluate the reproducibility of the Glu C digestion from day to day, HK standards and plasma (plasma citrate+ PI) samples were digested on three consecutive days, and MRM analysis was performed to detect peptides of interest (see Table 6A and Table 6B below). All peptides of interest were present in the HK standard and plasma samples with the indicated peak intensities. Table 6A and Table 6B. Each of the three days of the Glu C digestion data for HK standard and plasma (Plasma citrate+PI) had consistent results.

TABLE 6A

HK digested with Glu C on three consecutive days

| HK-Sigma digestion | SSRIGE Peak intensity | KKIYPTVNCQPLGMISLMK Peak intensity | SYYFDLTDGLS Peak intensity |
|---|---|---|---|
| Day1 | 3660 | 700 | 4.9 E4 |
| Day2 | 3900 | 920 | 4.5 E4 |
| Day3 | 3000 | 1200 | 4.8 E4 |

TABLE 6B

Plasma citrate + PI digested with Glu C on three consecutive days

| Plasma citrate + PI digestion | SSRIGE Peak intensity | Long HK peptide Peak intensity | SYYFDLTDGLS Peak intensity |
|---|---|---|---|
| Day1 | 720 | 1.5 E4 | 3000 |
| Day2 | 750 | 1.4 E4 | 2200 |
| Day3 | 440 | 1.7 E4 | 2173 |

(xi) Ratios between SSRIGE (SEQ ID NO: 5) and SYYFDLTDGLS (SEQ ID NO: 10)

a. Calculating ratios of SSRIGE (SEQ ID NO: 5) and SYYFDLTDGLS peptide (SEQ ID NO: 10)

Glu C-digested HK and plasma samples were used to calculate the ratio between SSRIGE (SEQ ID NO: 5) and SYYFDLTDGLS (SEQ ID NO: 10) peptides by targeted assay (MRM) in normal plasma vs plasma from individuals with HAE. Measuring the ratio of SSRIGE (SEQ ID NO: 5) peptide against a HMWK unique peptide may be used, for example, in a diagnostic assay. All the ratios and average ratios were calculated by taking area under the peak of peptide in quantitation using Analyst® software.

Figure 5:
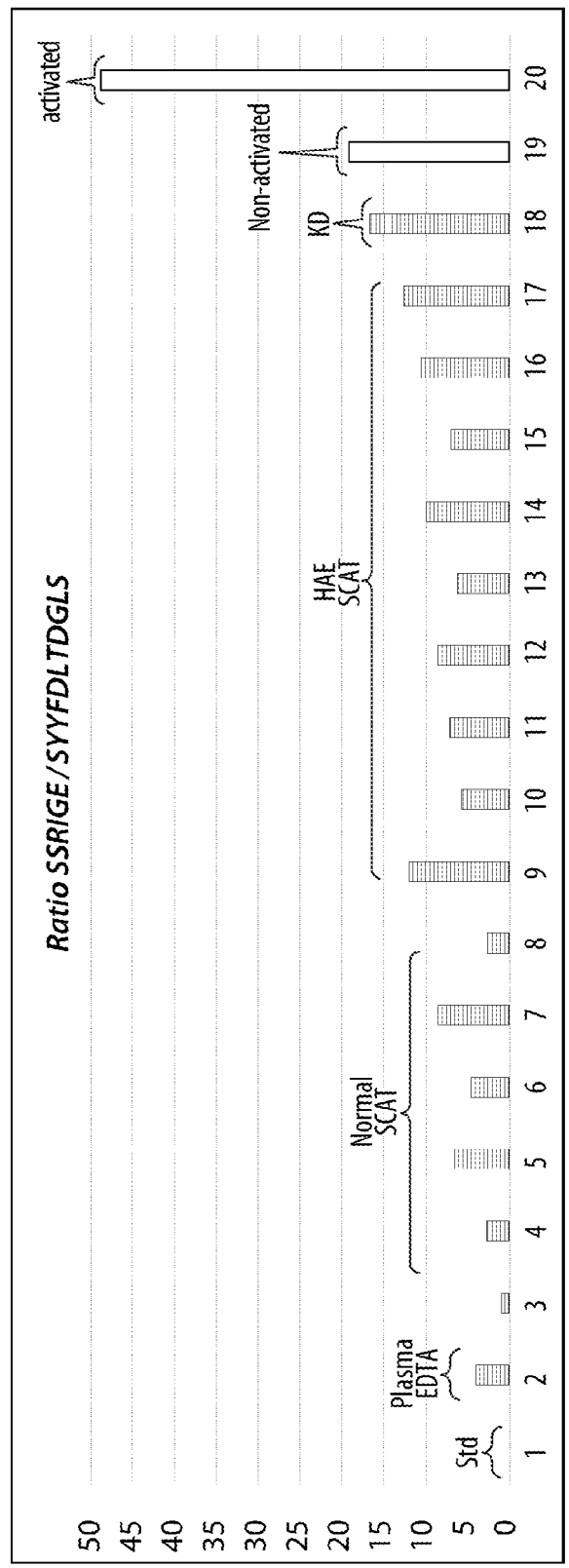
FIG. 5 is a chart showing the ratios of SSRIGE (SEQ ID NO: 5)/SYYFDLTDGLS (SEQ ID NO: 10) in Glu C-digested HMWK and plasma samples.

An overall increase in the ratio of SSRIGE (SEQ ID NO: 5)/SYYFDLTDGLS (SEQ ID NO: 10) was observed in HAE SCAT plasma samples when compared with normal SCAT plasma samples. There was also a significant increase in the ratio of SSRIGE (SEQ ID NO: 5)/SYYFDLTDGLS (SEQ ID NO: 10) in the activated plasma versus the non-activated plasma (FIG. 5).

b. Average Ratios Between SSRIGE (SEQ ID NO: 5) and SYYFDLTDGLS Peptide (SEQ ID NO: 10)

Figure 6:
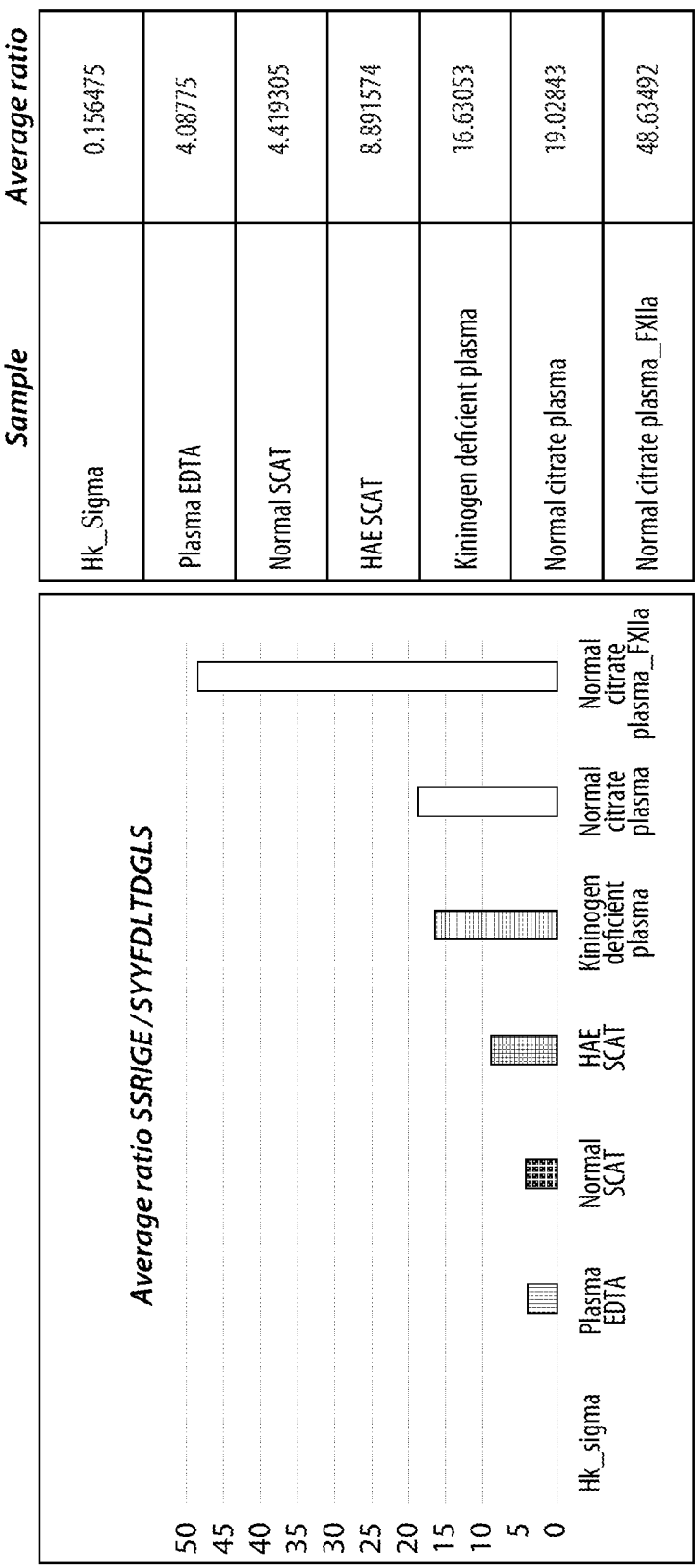
FIG. 6 is a chart showing the average ratio of SSRIGE (SEQ ID NO: 5)/SYYFDLTDGLS (SEQ ID NO: 10) using Area under the Curve of Peak.

The average ratio of SSRIGE (SEQ ID NO: 5)/SYYFDLTDGLS (SEQ ID NO: 10) was calculated in different sample types be the area under the peak using the MRM targeted assay (FIG. 6). The average ratios between SSRIGE (SEQ ID NO: 5)/SYYFDLTDGLS (SEQ ID NO: 10) were found to be higher in HAE SCAT plasma samples as compared to normal SCAT plasma samples. This ratio of SSRIGE (SEQ ID NO: 5) peptide against HMWK vs LMWK unique peptide SYYFDLTDGLS (SEQ ID NO: 10) has a potential to be used in an assay, such as for diagnosing a disease or disorder associated with cleaved kininogen or distinguishing between samples from healthy individuals and diseased individuals.

(xii) LC-MS Run Optimization Using HK Standard

In order to increase the efficiency of the method, the LC-MS runs were optimized by optimizing the gradient and shorten the run time. The LC-MS optimization was primarily performed using a HK standard. As shown in FIG. 6, the results of several methods are presented out of the various LC-gradients and run times used. The LC-MS method successfully shortened to 10 min runs. The bottom left chromatogram presents the "optimized method" as the SYYFDLTDGLS peptide (SEQ ID NO: 10) appears as a single peak instead of a split peak. Both peptides, SSRIGE (SEQ ID NO: 5) and SYYFDLTDGLS (SEQ ID NO: 10), necessary for the ratio calculation were found with a significant reduction in run time.

(xiii) LC-MS Run Optimization Using Plasma Samples

The shorter LC-MS run described above was validated using plasma samples, in which the peptides of interest (SSRIGE (SEQ ID NO: 5) and SYYFDLTDGLS (SEQ ID NO: 10)) were detected. Detection of the peptides of interest in both HK standard and plasma samples were detected using a 16.5 min run method, which is a significant improvement over the original methodology (42 mins). The intensities of both peptides decreased as the complexity of the plasma sample increased: EDTA plasma>Citrated plasma>SCAT plasma.

Example 2: Quantitation of the 46 kDa Light Chain of Cleaved HWMK in HAE Plasma Using Signature Peptide and LC-MS/MS The exemplary method described in this example was designed to determine endogenous 2-Chain HMWK (which may be represented by the level of the 46 kDa light chain) concentration in human plasma. The method involves crashing 25 μL of plasma followed by pellet digestion and further purification using MCX SPE and analyzed by liquid chromatography-tandem mass spectrometry (LC-MS/MS). The two dimensional HPLC (Agilent Metasil AQ C18 Column, 5.0 μm, 2.1 mm×100 mm (C/N A0530100X020) and AB Sciex QTrap 6500 mass spectrometer were operated in the Selected Reaction Monitoring (SRM) mode under optimized conditions for detection of a signature peptide of 2-Chain HMWK, H$_2$N-KHNLGHGH-OH (SEQ ID NO: 1) and Stably labelled internal standard (SLIS) (KHNL[$^{13}$C$_6$]GHGH) using positive ions formed by electrospray ionization.

An aliquot of 25 µL human plasma was mixed with 2.5 µL of 10% SDS, 5 µL of DTT (500 mM) and proteins were reduced at 37° C. for 60 minutes. To the solution was sequentially added 75 µL and 600 µL methanol to precipitate the proteins. The supernatant was discarded and the protein pellets were washed again with 700 µL methanol. After centrifuge, the pellets were reconstituted in 500 µL of ammonium bicarbonate buffer (100 mM) with strong vertex for 10 minutes. An aliquot solution of 25 µL internal standard (KHNL[$^{13}$C$_6$]GHGH, 30 ng/mL) and 5.0 µL of iodoacetamide solution (500 mM) were added and the mixture is kept in dark for 30 minutes. Proteins were subsequently digested by adding 10 µL of chymotrypsin (8 mg/mL) and retaining at 50° C. for 3 hours with gentle vortex.

The resulting mixture was acidified and loaded to a MCX 96-well cartridge (30 µm, 10 mg) for desalting. The cartridge was washed with 900 µL of 2.0% formic acid solution, 900 µL water, and 900 µL of methanol, respectively, and the resulting peptides were eluted with 600 µL of –5.0% ammonia hydroxide in methanol. The eluted solution was dried in nitrogen gas and reconstituted in 100 µL of methanol:water (10:90; v/v) containing 1.0% HFBA.

For sample analysis, the peptides were loaded to an LC-MS/MS instrument operated in the MRM mode, where the ion intensities of signature peptide KHNLGHGH (SEQ ID NO: 1) and its internal standard KHNL[$^{13}$C6]GHGH were recorded. The relative amount of 46 kDa light chain of the 2-chain HMWK in plasma samples was calculated accordingly.

(i) Assay Validation (Precision and Accuracy):

The intra-day (n=6) and inter-day (n=18) precision (% R.S.D.) and accuracy (% RE) to quantitate 46 kDa light chain in human plasma (SCAT169) were determined using the method described herein. As shown in Table 7 below, the levels of 46 kD determined in both the intra-day and inter-day assays using the methods described herein are very close to the theoretical concentration of the 46 kD in tested samples. These results indicate the accuracy of the assay methods described herein, using the 46 kDa light chain signature peptide noted above as a biomarker.

TABLE 7

The intra-day (n = 6) and inter-day (n = 18) precision (% R.S.D.) and accuracy (% RE) to quantitate the 46 kDa light chain in human plasma (SCAT169)

| Analyte | Theoretical conc (ng/mL) | Intra-day Measured conc ± S.D. (µg/mL) | R.S.D. (%) | RE (%) | Inter-day Measured conc ± S.D. (µg/mL) | R.S.D. (%) | RE (%) |
|---|---|---|---|---|---|---|---|
| 46 KD light chain | 2.08 (EL) | 1.97 ± 0.162 | 8.2 | –5.3 | 2.04 ± 0.176 | 8.6 | –1.9 |
|  | 2.28 (LLQC) | 1.98 ± 0.056 | 2.8 | –13.2 | 2.00 ± 0.123 | 6.2 | –12.3 |
|  | 2.68 (LQC) | 2.42 ± 0.303 | 12.5 | –9.7 | 2.31 ± 0.293 | 12.7 | –13.8 |
|  | 7.08 (MQC) | 6.86 ± 0.509 | 7.4 | –3.1 | 6.49 ± 0.594 | 9.1 | –8.3 |
|  | 17.1 (HQC) | 17.2 ± 0.367 | 2.1 | 0.6 | 16.5 ± 0.957 | 5.8 | –3.5 |

(ii) Stability Assessment

Human plasma samples were collected in SCAT169 tubes following the methods described herein. The samples have gone through four freeze-thaw cycles or kept on bench top (4° C.) for 8 hours. The assay methods described above, using the 46 kDa light chain signature peptide, were performed to measure the level of the 46 kD light chain in both samples. The results thus obtained show that the 2-chain HMWK (represented by the 46 kDa light chain) are stable in human plasma samples. Table 8.

TABLE 8

Stability testing of 2-Chain HMWK in human plasma (SCAT169) (n = 3)

| Analyte | Stability | Theoretical conc. (µg/ml) | Measured conc. ± S.D. (µg/ml) | R.S.D. (%) | Relative error (%) |
|---|---|---|---|---|---|
| 2HK | Four freeze-thaw cycle | 2.68 | 2.44 ± 0.158 | 6.5 | –9.0 |
|  |  | 17.1 | 15.6 ± 0.450 | 2.9 | –8.8 |
|  | Bench top (4° C., 8 h) | 2.68 | 2.49 ± 0.143 | 5.7 | –7.1 |
|  |  | 17.1 | 15.8 ± 0.346 | 2.2 | –7.6 |

(iii) Application of Assay Method in Disease Diagnosis and Prognosis

Figure 7:
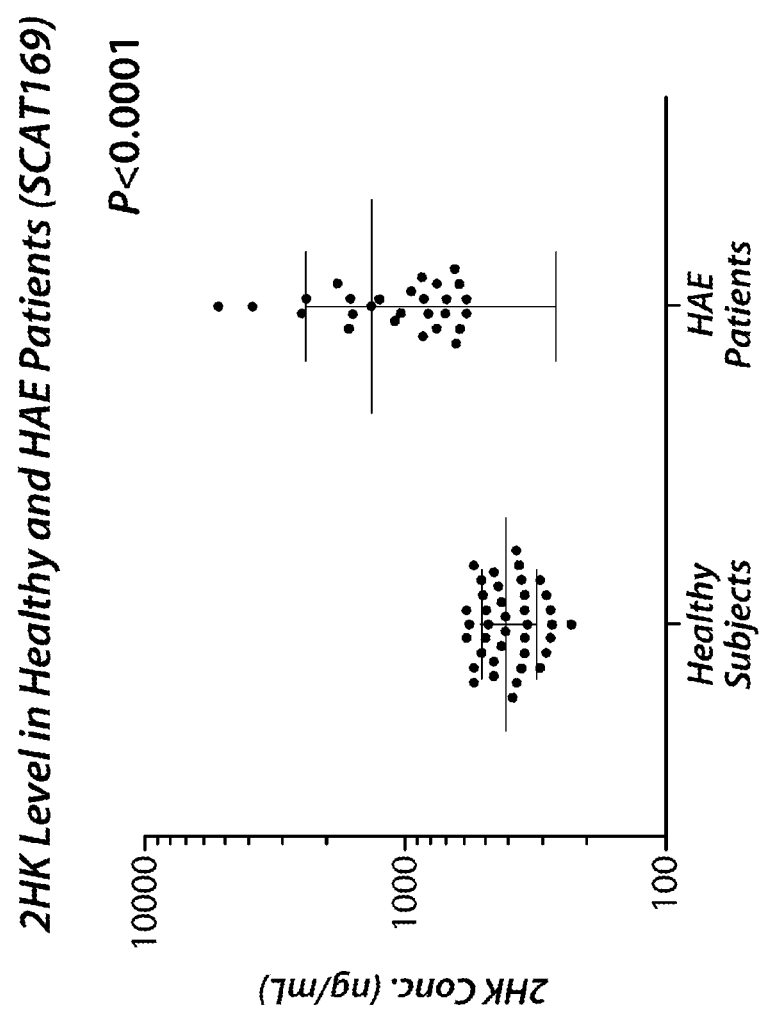
FIG. 7 is a chart showing the concentration of cleaved HMWK (represented by the 46 kDa light chain) for differentiating HAE patients from healthy individuals

Plasma samples were collected from healthy human subjects and HAE patients in SCAT169 tubes. The assay method described above was performed to measure the 2-chain HMWK level in these human plasma samples. As shown in FIG. 7, the level of 2-chain HMWK in HAE patients was significantly higher than that in healthy human subjects. The results indicate that 2-chain HMWK, as well as any components thereof (e.g., the 46 kDa light chain), can serve as a reliable biomarker for HAE diagnosis and/or prognosis.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of examples only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for detecting cleaved high molecular weight kininogen (HMWK) in a sample, the method comprising:
   (i) providing a sample suspected of containing HMWK,
   (ii) contacting the sample with a protease to generate a plurality of digested peptides; and
   (iii) measuring the level of a signature peptide indicative of the 46 kDa light chain or 56 kDa light chain of cleaved HWMK in the plurality of digested peptides, wherein the signature peptide indicative of the 46 kDa light chain is:

KHNLGHGH, (SEQ ID NO: 1)

KHNLGHGHKHE; (SEQ ID NO: 2)

KHNLGHGHK; (SEQ ID NO: 3)
   or

KHNLGHGHKHER; (SEQ ID NO: 4)

or,
   wherein the signature peptide indicative of the 56 kDa light chain is SSRIGE (SEQ ID NO: 5).

2. The method of claim 1, wherein the protease is selected from the group consisting of chymotrypsin, endoproteinase Glu-C, endoproteinase Asp-N, cathepsin G, and endoproteinase Lys-C.

3. The method of claim 1, further comprising measuring the level of a signature peptide that is indicative of full-length HMWK.

4. The method of claim 3, wherein the signature peptide indicative of full-length HMWK is:

GHEKQRKH; (SEQ ID NO: 6)

KQRKHNLGHGHKHE; (SEQ ID NO: 7)

DWGHKQRKHNLGHGHKHER; (SEQ ID NO: 17)

HNLGHGHK; (SEQ ID NO: 9)
   or

SYYFDLTDGLS. (SEQ ID NO: 10)

5. The method of claim 3, wherein the level of the signature peptide indicative of cleaved HMWK, the level of the signature peptide indicative of full-length HMWK, or both are measured by liquid chromatography-mass spectrometry (LC-MS).

6. The method of claim 1, wherein the sample is a biological sample obtained from a human subject.

7. The method of claim 6, wherein the human subject has or is suspected of having hereditary angioedema (HAE).

8. The method of claim 6, wherein the biological sample is a plasma sample collected in an evacuated blood collection tube, which comprises a liquid formulation that comprises a mixture of protease inhibitors.

9. The method of claim 1, wherein step (ii) is performed in the presence of a reducing agent.

10. The method of claim 6, further comprising determining whether the human subject has hereditary angioedema (HAE), wherein an elevated level of cleaved HMWK in the biological sample obtained from the human subject as compared with a predetermined reference value indicates that the human subject has HAE.

11. The method of claim 6, further comprising determining whether the human subject is at risk for hereditary angioedema (HAE) attack; wherein an elevated level cleaved HMWK in the biological sample obtained from the human subject as compared with a predetermined reference value indicates that the human subject is at risk for HAE attack.

12. The method of claim 6, wherein the biological sample is a blood sample or a plasma sample.

13. The method of claim 8, wherein the evacuated blood collection tube is a SCAT tube.

14. The method of claim 1, wherein step (ii) is performed in the absence of a protease inhibitor, an anticoagulant, or both the absence of a protease inhibitor and an anticoagulant.

* * * * *